United States Patent [19]

Rotwein et al.

[11] Patent Number: 4,963,665

[45] Date of Patent: Oct. 16, 1990

[54] HUMAN PREPROINSULIN-LIKE GROWTH FACTOR I

[75] Inventors: Peter S. Rotwein, St. Louis; Gwen G. Krivi, Olivette, both of Mo.

[73] Assignee: Washington University, St. Louis, Mo.

[21] Appl. No.: 929,671

[22] Filed: Nov. 20, 1986

Related U.S. Application Data

[63] Continuation-in-part of Ser. No. 816,662, Jan. 7, 1986, abandoned.

[51] Int. Cl.$^5$ .................... C07H 21/04; C12N 15/00
[52] U.S. Cl. .......................................... 536/27; 435/6; 435/69.4; 435/172.3; 435/235; 435/252.33; 435/317.1; 435/320; 514/2; 530/303; 530/324; 530/399
[58] Field of Search .................... 435/172.3, 320, 70, 435/317.1; 530/324, 303; 536/27

[56] References Cited

PUBLICATIONS

Jansen et al., 1983, Nature, 306:609–611.
Bell et al., 1985 (Oct.), PNAS 82:6450–6454.
Rotwein et al., 1986, J. Biol. Chem., 261:4828–4832.
Rotwein, 1986, PNAS, 83:77–81.
Ernst Rinderknecht and Rene E. Humbel, *J. Biol. Chem.*, 253:2769 (1978).

*Primary Examiner*—Charles F. Warren
*Assistant Examiner*—P. Rhodes
*Attorney, Agent, or Firm*—James W. Williams, Jr.; Carol H. Clayman

[57] ABSTRACT

The invention provides DNA sequences encoding a human preproinsulin-like growth factor I protein and novel extension peptides. A novel preproinsulin-like growth factor I protein and novel extension peptides are also provided. The present invention further provides a human IGF-I gene which has been sequenced and which encodes at least two preproinsulin-like growth factor-I proteins. Various genes and DNA sequences useful in producing essentially pure mature IGF-I, preproinsulin-like growth factor I proteins and IGF-I gene related proteins are also provided.

18 Claims, 19 Drawing Sheets

```
         10         20         30        40         50         60
CTTCTGTGTTTGCTAAATCTCTCACTGTCTAAATTCAGAGCAGATAGAGCCTGCGCAAT
       ###
         70         80         90        100        110        120
GGAATAAAGTCCTCAAAATTGAAATGTGACATTGCTCTCAACATCTCCATCTCTCTGA
                      ***
        130        140        150        160        170        180
TTTCCTTTTGCTTCATTATTCCTGCTAACCAATTCATTTTCAGACTTTGTACTTCAGAAG 190        200        210        220        230        240
CAATGGGAAAAAATCAGCAGTCTTCCAACCCAATTATTTAAGTGCTGCTTTTGTGATTTCT
           MetGlyLysIleSerSerLeuProThrGlnLeuPheLysCysCysPheCysAspPheL 250        260        270        280        290        300
TGAAGGTGAAGATGCACACCATGTCCTCTCGCATCTCTTCTACCTGGCGCTGTGCCTGC
euLysValLysMetHisThrMetSerSerHisLeuPheTyrLeuAlaLeuCysLeuL 310        320        330        340        350        360
TCACCTTCACCAGCTCTGCTGTGGAGACCGGAGACGCTCTGCCGGGGGCTGAGCTGGTGG
euThrPheThrSerSerAlaThrAlaGlyProGluThrLeuCysGlyAlaGluLeuValA 370        380        390        400        410        420
ATGCTCTTCAGTTCGTGTGTGGAGACAGGGGCTTTTATTTCAACAAGCCCACAGGGTATG
spAlaLeuGlnPheValCysGlyAspArgGlyPheTyrPheAsnLysProThrGlyTyrG 430        440        450        460        470        480
GCTCCAGCAGTCGGAGGGCGCCTCAGACAGGCATCGTGGATGAGTGCTGCTTCCGGAGCT
lySerSerArgArgAlaProGlnThrGlyIleValAspGluCysCysPheArgSerC
```

FIGURE 2.

```
      490         500         510         520         530         540
GTGATCTAAGGAGGCTGGAGATGTATTGCGCACCCTCAAGCCTGCCAAGTCAGCTCGCT
ysAspLeuArgArgLeuGluMetTyrCysAlaProLeuLysProAlaLysSerAlaArgS
         550         560         570         580         590         600
CTGTCCGTGCCCAGCGCCACCGACATGCCCAAGACCAAGAGTATCAGCCCCCATCTA
erValArgAlaGlnArgHisThrAspMetProLysThrLysTyrGlnProProSerT
         610         620         630         640         650         660
CCAACAAGAACACGAAGTCTCAGAGAAGGAAAAGGTTGGCCAAAGACACATCCAGGAGGGG
hrAsnLysAsnThrLysSerGlnArgArgLysGlyTrpProLysThrHisProGlyGlyG
         670         680         690         700         710         720
AACAGAAGGAGGGGACAGAAGCAAGTCTGCAGATCAGAGGAAAGAAGAAAGAGACAGAGGA
luGlnLysGluGlyThrGluAlaSerLeuGlnIleArgGlyLysLysLysGluArgA
         730         740         750         760         770         780
GGGAGATTGGAAGTAGAAATGCTGAATGCAGAGGCAAAAAAGGAAAAATGAAGGACAGGAG
rgGluIleGlySerArgAsnAlaGluCysArgGlyLysGlyLysLysGlyLys***
         790         800         810         820         830         840
GATTAAACAGAGGCAAGGATGATGAGAGGAGCAGCAAGAATGAAAAGCAG
         850         860         870         880         890         900
AAAATACAATAGAGGAAATGAAGAAAAGTAGGCCTGCTGGAGCTAGATGATGATGTGATG
         910         920         930         940         950         960
GAAATAGAAGTAACCTTTTAGAGAATCTGCTAAGAAAACATGGAGAAAACGGAAAAGAAA
```

FIGURE 2. CONTINUED

```
       970       980       990      1000      1010      1020
AATGTAATGCCCTAGAAAGCGGCAAAGAAAGACAGTGGCAAAATGAAAAAAAAATAA
      1030      1040      1050      1060      1070      1080
AAATTATAAAGAGGCAAAAAAGACACACTATTCTCTGCCCCTCTAAACACAATTAAAT
      1090      1100      1110      1120      1130      1140
AAAAGAATTTAAATAAAAAAAAAAAAAAAAAAAAAAAAAAAAAAAAAAAAAA
```

FIGURE 2. CONTINUED

```
                    ┌─────── EXON 1 ───────
GAATTCTCAATGGCAAAGGCAAGTGTACATTATAAATAGCAAAACAGCTGGCTTGGAACC    60

TGTTGCCGGCCAGTCACCCAGTTGAGGGATTTGAATGACATCATAACCCTCAAGAGGGTA   120

TTGCTAGCCAGCTGGTGTGTTATTTAGAATACAAAAATCAGAGAAAGAAAACACACTCTG   180

GCACACAGACTCCCTCTGTCATACACACACACACACACACACACACACACACACACACAC   240

AGAGGTTTGAGTTATATGGAAAATTCAAACAACAGGAAAATTGTTTGCCCCCAGGTACC    300

CTTCTCCCAGAGTGGTGGGGGTGGGGAGGGGACAGTGACAGGCAGCCTAGTAGAAGAATAA  360

AGAAAAATGTTCTATTTCAGTTGGGTTTTACAGCTCGGCATAGTCTTTGCCTCATCGCAG  420

GAGAAAAGTATGAGACAGTGCCCTAAAGGACCAATCCAATGCTGCCTGCCCCCTCCATA   480

GGTTCTAGGAAATGAGATCACACCCCTCACTTGGCAACTGGGACAAGGGTCACCCGAGT   540
                                                       ^^
GCTGTCTTCCAATCTACTTTACCCCAGTCACTTCAGGGTTAAAATTGTAGAGTTTGCTGG   600

AGAGGGTCTTATCGTCCTTTCTTTCTTTTTTGTTTTAATAATGCATTTGCTCTAGAAT    660

CTAAAATTGCTCTCCCATCCCCCATATTCCTTTAATACTGGTAAGGTGTATTAGCAGACG  720

TTTGTGTCTTCATGCCCAGCAGAAAGTTAATCAGAAAACAGATCCTTATTTTCTATGGCA  780

GCATAAGTATTTTAAATGTCTGCGAACCCTGTCACTAACACACATTCTTTTAAGGAAAAA  840

FIGURE 4.
```

```
AATGCTTCTGTGCTCTAGTTTTAAAATGCAAAGGTATGATGTTATTTGTCACCATGCCCA 900
AAAAGTCCTTACTCAATAACTTTGCCAGAGAGGGAGAGAGAGAAGCAAATGTTCC 960
CCCAGCTGTTCCTGTCTCTACAGTGTCTGTGTTTTGTAGATAAATGTGAGGATTTCTCTA 1020
AATCCCTCTTCTGTTTGCTAAATCTCACTGTCACTGCTAAATTCAGAGCAGATAGAGCCT 1080
                                    ***
GCGCAATGGAATAAAGTCCTCAAAATTGAAATGTGACATTGCTCTCAACATCTCCCATCT 1140
                                ***
CTCTGGATTTCTTTTTTGCTTCATTATTCCTGCTAACCAATTCATTTTCAGACTTTGTACT 1200
TCAGAAGCAAATGGGAAAAATCAGCAGTCTTCCAACCCAATTATTTAAGTGCTGCTTTTGT 1260
                                            MetGlyLysIleSerSerLeuProThrGlnLeuPheLysCysPheCys
       .....4.5 kb.....
GATTTCTTGAAGgtaaatatttctactctttgaagtcattggggaattc..........1310
AspPheLeuLys ..................................................ggatcccact 1320
gtaatatagcatcttcattccgtagtaaacgtttctagatatttttgtctcaattcat 1380
tgaaataggaaccataaagaaagggttcaggaggactcctccaaagatccacagtag 1440
ccaggggaataaacacaggttgtgatgccgagacacgctccatcctgatcctgct 1500
gggttctcatgtactctattggcttctgtgctgtgtagtcctgattaatgacagtcgtgg 1560
aatcgtgggagtcaatgcacttctgtcccaccactccccttgcaaggatcaaggagga 1620
```

FIGURE 4. CONTINUED

```
                              ─────── EXON 2 ───────
aacctgaacctccctctgtttcttgggcagGTGAAGATGCACCACCATGTCCTCCTCGCAT 1680
                               ValLysMetHisThrMetSerSerHis CTCTTCTACCTGGCGCTGTGCCTGCTCACCTTCACCTTCCACCGCTCTGCCACGGCTGACCGCGAG 1740
LeuPheTyrLeuAlaLeuCysLeuLeuThrPhoThrSerSerAlaThrAlaGlyProGlu
                                                          ─ ─ ─ ─ ─

ACGCTCTGCGGGCTGGAGCTGGATGCTCTTCAGTTCGTGTGTGGAGACAGGGCTTT 1800
ThrLeuCysGlyAlaGluLeuValAspAlaLeuGlnPheValCysGlyAspArgGlyPhe
─ ─ ─ ─ ─ ─ ─ ─ ─ ─ ─ ─ ─ ─ ─ ─ ─ ─ ─ ─ ─ ─ ─ ─

TATTTCAgtaagtagccctccctctcaatgtgctgctgctcaagtctaaagtgtacagct 1860
TyrPheA
─ ─ ─ ─ ─ ctgtggatttacaaccgcagggagtgtgtgaataactgaatgagtgcccgtatctggcag 1920
ccatcctaggcctctcgagattcctcgacctttaaagtaagcatagtgttttggcgggactt 1980
tggcaggttttgcagatct.........         >21 kb.        .........2009
ggtgaatgagttagtgctaatgagtgtgtacagactccgggagacatactggcattcag 2069
aaagatacgtggggtcaggaatcattggggaagtttcaagaagaggttgagacattgcag 2129
aatatgtaggttgactagctgtggggagaggcaggaggcaggggtggaagactgaagaaagc 2189
```

FIGURE 4. CONTINUED

```
agattgcacccctaacatgaggccactctgtttgattgtgcagACAAGCCCACAGGTAT 2249
                                            snLysProThrGlyTyr
                                            |―――EXON 3―――

GGCTCCAGCAGTCGGAGGGCGCCTCAGACAGGCATCGTGGATGAGTGCTGCTTCCGGAGC 2309
GlySerSerArgArgAlaProGlnThrGlyIleValAspGluCysCysPheArgSer
―――――――――――――――――――――――――――――――――――――――――――――――――――――――――

TGTGATCTAAGGAGGCTGGAGATGTATTGCGCACCCCTCAAGCCTGCCAAGTCAGCTCGC 2369
CysAspLeuArgArgLeuGluMetTyrCysAlaProLeuLysProAlaLysSerAlaArg
―――――――――――――――――――――――――――――――――――――――――――――――――――――――――

TCTCTCCGTGCCCAGCGCCACACCGACATGCCCAAGACCCAGAAGgtaagcccacctggg 2429
SerValArgAlaGlnArgHisThrAspMetProLysThrGlnLys
―――――――――――――――――――――――――――――――――――――――――――――| tgggatc. . . . . . . . 1.3 kb. . . . . . . . . . . . . . . . . . . . 2437
ccagtgaccacgcctcttgtttctaactgggaggggtagtgtcaagagatgagtcccaaa 2497
gttctgaatggtgggtcttgtgactgaggtctagacccctccagcatgatgctgtct 2557
ccatcatcatgagcctgggcattctgagctcattcaaaggacaccatgggaaccac 2617
                                                     |―――EXON 4―――
                                                          1B ttgttctcaatgcaattattttgatgttacagTATCAGCCCCATCTACCAACAAG 2677
                                 TyrGlnProSerThrAsnLys
```

FIGURE 4. CONTINUED

```
AACACGAAGTCTCAGAGAAGGAAAGGTTGGCCAAAGACACATCCAGGAGGGAACAGAAG 2737
AsnThrLysSerGlnArgArgLysGlyTrpProLysThrHisProGlyGlyGluGlnLys

GAGGGGACAGAAGCAAGTCTGCAGATCAGAGAAAGAAGAGCAGAGAGGAGATT 2797
GluGlyThrGluAlaSerLeuGlnIleArgGlyLysLysLysGluGlnArgArgGluIle

GGAAGTAGAAATGCTGAATGCAGAGGCAAAAAGGAAAATGAAGGACAGGAGGATTAAAC 2857
GlySerArgAsnAlaGluCysArgGlyLysGlyLysLysGlyLys***

AGACAGAGGCAAGGATGATGAGAGAGGAGACACGAAGAATGAAAAGCAGAAATACA 2917
ATAGAGGAAATGAAGAAAAGTAGGCCTGCTGGAGCTAGATGATGTGATGGAAATAGA 2977
AGTAACCTTTTAGAGAATCTCGCTAAGAAACATGGAGAAACGGAAAAAAAAATGTAAT 3037
GCCCTAGAAAGCGCAAAAGAAAGACAGTGGCAAAATGAAAAAAAAATAAAATTATAA 3097
AAGAGGCAAAAAAGACACACTATTCTCTGCCTCTAAAACACAATTAAATAAAAGAATTT 3157
AAATAAAAttaaggcttctatatgcatttttaatttgtgaatctgttatggaaga 3217
polyA^
attgcctatgtcaatatatgttcagagttaaatattagccccaaatgctcagcaagactg 3277
```

FIGURE 4. CONTINUED

```
aattgtgtcatagaagttcccagattccctttcccgcaatgtcattgaggctgcattt 3337
cttagcaagtccaggtttaggcc........15kb.............         3361
ctgtgatgaagcagatgaatcaactctactttgtgtgattataaagctgtctggtat 3421
tcacgccaccaggtacatagaagatgcctgagtgaggttttgggaaaagtactaagg 3481
cctgtccacctatacatgccctctcaggaaaaccaagttcaagctctctattagctca 3541
actggtaaggcgtaagacatggaaggttgaggcccaatgttagaaatagatgatacata 3601
                                         ——— EXON 5 ———
                                         ——— 1A ———
                                          GluValHisLeuLysAs
aaacttcatcaagttaatgtcacttttctccttattctattatagGAAGTACATTTGAAGAA 3661
CGCAAGTAGAGGGAGTGCAGGAAACAAGAACTACAGGATGTAGGAAGACCCTCCTGAGGA 3721
nAlaSerArgGlySerAlaGlyAsnLysAsnTyrArgMet***
GTGAAGAGTGACATGCCACCGAGGATCCTTTGCTCTGCACGAGTTACCTGTTAAACTTTG 3781
GAACACCTACCAAAAAATAAGTTTGATAACATTGTCTTTAGGAGTGATTGCACCTTGCAAAAATGGT 3841
ATACACAAGTAAACATTCCAACATTGTCTTTAGGAGTGATTGCACCTTGCAAAAATGGT 3901
CCTGGAGTTGGTAGATTGCTGTGTTGATCTTTTATCAATAATGTTCTATAGAAAAGAAAAAATGGT 3961
AAATATATATATATATATATATATATCTTAgtccctgcctctcaagagccacacaatgccatggg 4021
                 polyA^
         FIGURE 4. CONTINUED
```

```
tgttgtatagatccagttgcactaaattcctctctgaatcttggctgctggagccattca 4081
ttcagcaacctgtctaagtggtttatgattgttcctatttgcacttcttctacac      4141
aactcgggctgttgtttacagtgtctgataatctgtagtctatacccaccacctcc     4201
cttcatacctttatatttgccgaatttggcctcctcaaagcagcaagcagtcgtcaag   4261
aagcacaccaattctaaccacaagattccatctgtggcatttgtaccaaatataagttg  4321
gatgcattttatttttagacacaaagcttt..........                     4349
```

FIGURE 4. CONTINUED

```
         10        20        30        40        50        60
x  CTTCTGTGTTTGCTAAATCTCACTGTCACTGTCTAAATTCAGAGCAGATAGAGCCTGCGCAAT
         70        80        90       100       110       120
   GGAATAAAGTCCTCAAAATTGAAAATGTGACATTGCTCTCAACATCTCCCATCTCTCTGGA
        130       140       150       160       170       180
   TTTCCTTTTTGCTTTCATTATTCCTGCTAACCAATTCATTTTCAGACTTTGTACTTCAGAAG
                                                          :::::::
                                                          TTTTTGCTTTCATTATTCCTGCTAACCAATTCATTTTCAGACTTTGTACTTCAGAAG
   x       10        20        30        40        50
        190       200       210       220       230       240
   CAATGGGAAAAATCAGCAGTCTTCCAACCCAATTATTTAAGTGCTGCTTTTTGTGATTTCT
   ::::::::::::::::::::::::::::::::::::::::::::::::::::::::::::
   CAATGGGAAAAATCAGCAGTCTTCCAACCCAATTATTTAAGTGCTGCTTTTTGTGATTTCT
           60        70        80        90       100       110
        250       260       270       280       290       300
   TGAAGGTGAAGATGCACACCATGTCCTCCTCGCATCTCTTCTACCTGGCGCTGTGCCTGC
   ::::::::::::::::::::::::::::::::::::::::::::::::::::::::::::
   TGAAGGTGAAGATGCACACCATGTCCTCCTCGCATCTCTTCTACCTGGCGCTGTGCCTGC
          120       130       140       150       160       170
```

FIGURE 5.

```
         310       320       330       340       350       360
TCACCTTCACCAGCTCTGCCACGGCTGGACCGGAGACGCTCTGCGGGGCTGAGCTGGTGG
:::::::::::::::::::::::::::::::::::::::::::::::::::::::::::
TCACCTTCACCAGCTCTGCCACGGCTGGACCGGAGACGCTCTGCGGGGCTGAGCTGGTGG
         180       190       200       210       220       230

370       380       390       400       410       420
ATGCTCTTCAGTTCGTGTGTGGAGACAGGGGCTTTTATTTCAACAAGCCCACAGGGTATG
:::::::::::::::::::::::::::::::::::::::::::::::::::::::::::
ATGCTCTTCAGTTCGTGTGTGGAGACAGGGGCTTTTATTTCAACAAGCCCACAGGGTATG
         240       250       260       270       280       290

430       440       450       460       470       480
GCTCCAGCAGTCGGAGGGCGCCCTCAGACAGGCATCGTGGATGAGTGCTGCTTCCGGAGCT
:::::::::::::::::::::::::::::::::::::::::::::::::::::::::::
GCTCCAGCAGTCGGAGGGCGCCCTCAGACAGGCATCGTGGATGAGTGCTGCTTCCGGAGCT
         300       310       320       330       340       350

490       500       510       520       530       540
GTGATCTAAGGAGGCTGGAGATGTATTGCGCACCCCTCAAGCCTGCCAAGTCAGCTCGCT
:::::::::::::::::::::::::::::::::::::::::::::::::::::::::::
GTGATCTAAGGAGGCTGGAGATGTATTGCGCACCCCTCAAGCCTGCCAAGTCAGCTCGCT
         360       370       380       390       400       410
```

```
       550       560       570       580       590       600
CTGTCCGTGCCCAGCGCCACACCGACATGCCCCAAGAGACCCAGAAGTATCAGCCCCATCTA
:::::::::::::::::::::::::::::::::::::::::::::::::::         :
CTGTCCGTGCCCAGCGCCACACCGACATGCCCCAAGACCCAAGAAGTACATTTGAA--
       420       430       440       450       460       470

610       620       630       640       650       660
CCAACAAGAACACGAAGTCTCAGAGAAGAAAGGTTGGCCAAAGACACATCCAGGAGGGG
                                  ::   ::::  :
           ------GAACGCAAGTAGAGGAGTGCAGGAAACAAGAAACTACAGGATGTAGG
                   480       490       500       510       520

670       680       690       700       710       720
AACAGAAGGAGG-GGACAGAAGCAAGTCTGCAGATCAGAGGAAAGAAAGAGCAGAGG
::  ::::: :       ::::         ::   :::
AAGACCCTCCTGAGGAGTGAAAGAGTGACACATGCCACCGCAGGATCCTTTGCTCTGCACGAG
                   530       540       550       560       570       580

730       740       750       760       770
AGGGAGA------TTGGAAGTAGAAATGCTGAATGCAGAGGCAAAAAGGAAAATGAAG
                 ::     ::      :::       :       ::::
TTACCTGTTAAACTTTGGAACACCTACCAAAAATAAGTTTGATAACATTTAAAAGATGG
590       600       610       620       630       640
```

```
         780            790            800            810             820            830
GACAGGAGGATT---AAACAGACAGAGGCAAGGATGATGAGAGAGGAGCAGAGCAGCAAGA
  ::            :::           ::          ::              ::

GCGTTCCCCCAATGAAATACACAAGTAAACATTCCAACATTGTTCTTTAGGAGTGATTT
         650            660            670             680            690            700

840            850            860            870             880            890
ATGAAAAGCAGAAAATACAATAGAGGAAATGAAGAAAAGTAGGCCTGCTGGAGCTAGATG
  :::  :::           :::  ::           ::           :: ::   ::

GCACCTTGCAAAAATGGTCCTGGAGTTGGTAGAT------TGCTGTTGATCTTTT
         710            720            730                      740           749

900            910            920            930             940            950
ATGATGTGATGGAAATAGAAGTAACCTTTTAGAGAATCTCGCTAAGAAACATGGAGAAAA
  ::             :::::         ::          ::          ::    ::::

ATCAATAATGTTCTATAGAAAAGAAAAAAAGAAAAAAATATATATATATATATCTTAAAAAA
         760            770            780             790            800            809

960            970            980            990            1000            1010
CGGAAAAGAAAAATGTAATGCCCTAGAAAGCGCAAAGAAAGACAGTGGCAAAAATGAAAA
  ::::

AAAAAAAA
      x
```

FIGURE 5. CONTINUED

```
         1020      1030      1040      1050      1060      1070
AAAAAAAATAAAAATTATAAAGAGGCAAAAAAGACACACTATTCTCTGCCCTCTAAAA
         1080      1090      1100      1110      1120      1130
CACAATTAAATAAAAGAATTTAAATAAAAAAAAAAAAAAAAAAAAAAAAAAAAAAAAA
         x
AAAAAAA
```

FIGURE 5. CONTINUED

NH₂-Met-Gly-Lys-Ile-Ser-Ser-Leu-Pro-Thr-Gln-Leu-Phe-Lys-Cys-Cys-Phe-Cys-Asp-Phe-Leu-
Lys-Val-Lys-Met-His-Thr-Met-Ser-Ser-Ser-His-Leu-Phe-Tyr-Leu-Ala-Leu-Cys-Leu-Leu-
Thr-Phe-Thr-Ser-Ser-Ala-Thr-Ala-Gly-Pro-Glu-Thr-Leu-Cys-Gly-Ala-Glu-Leu-Val-Asp-
Ala-Leu-Gln-Phe-Val-Cys-Gly-Asp-Arg-Gly-Phe-Tyr-Phe-Asn-Lys-Pro-Thr-Gly-Tyr-Gly-
Ser-Ser-Ser-Arg-Arg-Ala-Pro-Gln-Thr-Gly-Ile-Val-Asp-Glu-Cys-Cys-Phe-Arg-Ser-Cys-
Asp-Leu-Arg-Arg-Leu-Glu-Met-Tyr-Cys-Ala-Pro-Leu-Lys-Pro-Ala-Lys-Ser-Ala-Arg-Ser-
Val-Arg-Ala-Gln-Arg-His-Thr-Asp-Met-Pro-Lys-Thr-Gln-Lys-Tyr-Gln-Pro-Pro-Ser-Thr-
Asn-Lys-Asn-Thr-Lys-Ser-Gln-Arg-Arg-Lys-Gly-Trp-Pro-Lys-Thr-His-Pro-Gly-Gly-Glu-
Gln-Lys-Glu-Gly-Thr-Glu-Ala-Ser-Leu-Gln-Ile-Arg-Gly-Lys-Lys-Lys-Glu-Gln-Arg-Arg-
Glu-Ile-Gly-Ser-Arg-Asn-Ala-Glu-Cys-Arg-Gly-Lys-Lys-Gly-Lys-COOH

FIGURE 6.

HUMAN PREPROINSULIN-LIKE GROWTH FACTOR I

REFERENCE TO RELATED APPLICATIONS

This application is a continuation-in-part of co-pending application Ser. No. 816,662, filed Jan. 7, 1986, now abandoned.

The present invention relates to a novel insulin-like growth factor precursor protein and novel human preproinsulin-like growth factor I genes and DNA sequences.

BACKGROUND OF THE INVENTION

Insulin-like growth factors (IGF's) have been isolated from various animal species, and are believed to be active growth promoting molecules that mediate the anabolic effects of such hormones as growth hormone and placental lactogen. As such, IGF's should be useful in the treatment and/or potentiation of various growth conditions and/or wound healing.

The designation "insulin-like growth factors" was chosen to express the insulin-like effects and insulin-like structure of these peptides. IGF's share nearly 50% amino acid homology with insulin and in three dimensional structure resemble proinsulin. Furthermore, by three dimensional modeling, the structures of IGF's are similar to proinsulin being a single chain peptide, cross-linked by three disulfide bridges and consisting of a B-chain-like amino-terminal part (B domain), a connecting peptide (C domain), and an A-chain-like part (A domain). In addition, a carboxyl-terminal extension not found in proinsulin is present (D domain). Recent studies also report the presence of yet another carboxyl-terminal extension not found in proinsulin which has been given an E domain designation. The E domain peptide has thus far been identified in association with rat and human IGF-II. Hylka et al. (1985) and Zumstein et al. (1985).

To date, several classes of IGF's have been identified. These include IGF-I (Somatomedin C), IGF-II, Somatomedin A, and a mixture of peptides called multiplication-stimulating activity (MSA). This heterologous group of peptides exhibit important growth-promoting effects in vitro, Daughaday (1977); Clemmons and Van Wyk (1981a), and in vivo, van Buul-Offers and Van den Brande (1980), Schoenle et al. (1982).

Two human IGF's have been characterized. These are IGF-I, comprising a 70 amino acid basic protein, Rinderknecht and Humbel (1978a), Rubin et al. (1982), and IGF-II, comprising a 67 amino acid neutral peptide, Rinderknecht and Humbel (1978b); Marquardt and Todaro (1981). Whereas the complete amino acid sequences have only been determined for rat and human IGF-I and IGF-II, Humbel, R. E. (1984), a high degree of homology and/or cross-reactivity has been shown by radioimmunoassay and/or radioreceptor assay to exist among IGF-I's and among IGF-II's from different species. Wilson and Hintz (1982).

Circulating levels of these peptides appear to be under the control of growth hormone to a greater or lesser extent with IGF-I being controlled to a greater extent than IGF-II. IGF-I, for example, plays a fundamental role in postnatal mammalian growth as a major mediator of growth hormone action. See Copeland et al. (1980) and Schoenle et al. (1982).

Vassilopoulou-Sellin and Phillips (1982) have estimated, using molecular sieve chromatography, that IGF-I activity, assayed both in vitro and in vivo, extracted from rat liver has a higher molecular weight (approximately 30 kilodaltons) than activity extracted from plasma (approximately 8 kilodaltons). The authors suggested that the higher molecular weight material may represent an IGF-I precursor. The authors also demonstrated that metabolic regulation of the higher molecular weight rat liver IGF-I was similar to rat serum-derived IGF-I. Recently, Zumstein et al. (1985) isolated a variant pro-form of IGF-II from human serum which they demonstrated to contain IGF-II-like activity in vitro.

Because of the potential bioactivity and utility of high molecular weight, precursor IGF-I proteins in the treatment and/or potentiation of various growth conditions, the amino acid sequence and DNA coding sequence of such a precursor protein has long been sought.

Jansen et al. (1983), provided an amino acid sequence derived from a human IGF-I cDNA clone which supports the suggestion of a larger IGF-I precursor. See also Netherlands Patent Application No. 8302324, published Jan. 16, 1985. The cDNA disclosed by Jansen, however, did not provide sufficient DNA sequence information to teach the precise translational start of the suggested precursor protein. Additionally, Jansen et al. (1983) and Netherlands Patent Application No. 8302324 provide no evidence or teaching that the cDNA sequence is or can be expressed (e. g., that the suggested precursor protein is produced).

Indeed, very little is known about IGF-I biosynthesis. Preliminary studies suggest that only one human IGF-I gene exists per haploid genome. Ullrich et al. (1984); Brissenden et al. (1984); and Tricoli et al. (1984). Studies of IGF-I biosynthesis have been hampered by a very low IGF-I content in tissue, Vasilopoulou-Sellin and Phillips (1982) and because, in contrast to IGF-II, no cultured cell lines have been identified which elaborate significant quantities of this peptide. Clemmons and Van Wyk (1981b); Clemmons and Shaw (1983). Additionally, neither the complete human IGF-I gene has been isolated nor the complete DNA sequence determined. Preliminary studies by Bell et al. (1985) suggest that the human IGF-I gene is at least 35 kilobases (kb) in length, of which only 210 base pairs (bp) encodes mature human IGF-I. The studies by Bell et al. (1985) also suggest that the human IGF-I gene contains only four exons, which together encode a single precursor IGF-I protein. The large size (e.g. greater than 35 kb) and complexity of this gene relative to the mature IGF-I coding sequences has made both isolation and identification of the complete genomic DNA sequences extremely difficult. Isolation of a genomic IGF-I clone (e.g. IGF-I gene) would greatly facilitate studies of IGF-I biosynthesis and provide a means for identifying and producing precursor, mature and/or intermediate IGF-I species and allelic variants thereof. A genomic clone thus facilitates determining which proteins are believed to be active growth promoting peptides.

Accordingly, it is an object of this invention to provide a highly purified gene and/or synthetic DNA sequences encoding an IGF-I precursor protein (pre-proinsulin-like growth factor-I), and/or peptide fragments thereof and useful in making such a protein and/or fragments.

It is another object of this invention to provide processes utilizing such DNA in the production of such proteins and peptides.

Another object of this invention is to provide the amino acid sequence of a novel preproinsulin-like growth factor-I and methods using such a protein or fragments thereof to promote desirable growth or functionality of cells in animals.

SUMMARY OF THE INVENTION

The present invention relates to the discovery of a novel preproinsulin-like growth factor-I (ppIGF-I) protein, an essentially pure human IGF-I gene and synthetic DNA sequences which encode the novel ppIGF-I protein.

In one embodiment, the present invention provides an essentially pure IGF-I gene encoding at least two ppIGF-I proteins and containing the sequence of nucleotides (or their functional equivalents for protein expression) as given in FIG. 4.

In another embodiment, the invention provides synthetic DNA sequences encoding a novel ppIGF-I protein. One such synthetic DNA sequence contains the sequence of nucleotides (or their functional equivalents for protein expression) as given in FIG. 2.

In still another embodiment, the present invention provides an essentially pure DNA sequence encoding a carboxyl-terminal extension of the novel ppIGF-I protein. One such essentially pure DNA sequence contains the following sequence of nucleotides (or their functional equivalents for peptide expression):

5'TATCAGCCCCCATCTACCAACAAGAA
CACGAAGTCTCAGAGAAGGAAAGGTTG
GCCAAAGACACATCCAGGAGGGGAACA
GAAGGAGGGGACAGAAGCAAGTCTGCA
GATCAGAGGAAAGAAGAAAGAGCAGA
GGAGGGAGATTGGAAGTAGAAATGCTG
AATGCAGAGGCAAAAAAGGAAAATGA3'

In yet another embodiment, the invention provides a novel ppIGF-I protein having the amino acid sequence as given in FIG. 6.

In a further embodiment, the present invention provides a novel extension peptide having the following amino acid sequence:

NH$_2$—Tyr Gln Pro Pro Ser Thr Asn Lys Asn Thr Lys Ser Gln Arg Arg Lys Gly Trp Pro Lys Thr His Pro Gly Gly Glu Gln Lys Glu Gly Thr Glu Ala Ser Leu Gln Ile Arg Gly Lys Lys Lys Glu Gln Arg Arg Glu Ile Gly Ser Arg Asn Ala Glu Cys Arg Gly Lys Lys Gly Lys—COOH.

This extension peptide represents a carboxyl-terminal extension portion of the novel ppIGF-I protein.

In other embodiments, the invention provides various methods for promoting growth and/or other desirable functions of cells in animals by administering the novel proteins and/or peptides of this invention to animals in amounts sufficient to cause such effects.

In other embodiments, the present invention provides methods for producing the essentially pure proteins of this invention by causing expression of the gene and/or synthetic DNA sequences provided herein.

BRIEF DESCRIPTION OF THE DRAWINGS

In the following diagrammatic representations, amino acid sequences are provided reading from the amino terminus (NH$_2$) to the carboxy terminus (COOH) of the sequence. The DNA sequences are provided in a 5' to 3' orientation. Relevant restriction endonuclease sites are also shown. The DNA regions marked as described below are for purposes of diagrammatic representation only and are not drawn to scale unless otherwise noted. The numbering of the DNA sequences from 5' to 3' and of the amino acid sequences from the amino terminus to carboxy terminus is for diagrammatic purposes only.

FIG. 2 depicts the DNA sequence of the IGF-1B cDNA clone (1136 nucleotides) and a translation of the 585 base open reading frame starting at nucleotide 183 (e. g. ppIGF-1B amino acid sequence.) Termination codons are denoted by ### and ***. The broken underlined region denotes the nucleotides encoding the mature human IGF-I peptide (nucleotide 327 through nucleotide 536) and attendant amino acid sequence of mature human IGF-I. The solid underlined region denotes the nucleotides encoding the IGF-1B carboxyl-terminal extension peptide and attendant amino acid sequence of said extension peptide.

FIG. 4 depicts the DNA sequence of the human IGF-I gene. Exons are in upper case and introns and flanking DNA are in lower case. Translation of the ppIGF-I proteins (e.g. amino acid sequence of ppIGF-1A and ppIGF-1B) are indicated and carboxyl-terminal extensions of the ppIGF-1A and ppIGF-1B are denoted by solid overlines labeled 1A and 1B, respectively. The 70 amino acids of mature IGF-I are denoted by a broken underline. In frame translation termination codons, TGA and TAA, preceding the translation initiation start-signal codon, ATG, are denoted by ***. A putative transcription start site is denoted by ΛΛ. Polyadenylation signals AATAAA and AATATA are denoted by a solid overline and are followed by poly A addition sites, denoted "poly AA", in exons 4 and 5, respectively. The dotted line denotes unsequenced regions the lengths of which are marked thereon in kb (kilobases).

FIG. 5 depicts a comparison of the IGF-1A and IGF-1B cDNA sequences. The top line represents IGF-1B.

Figure 1:
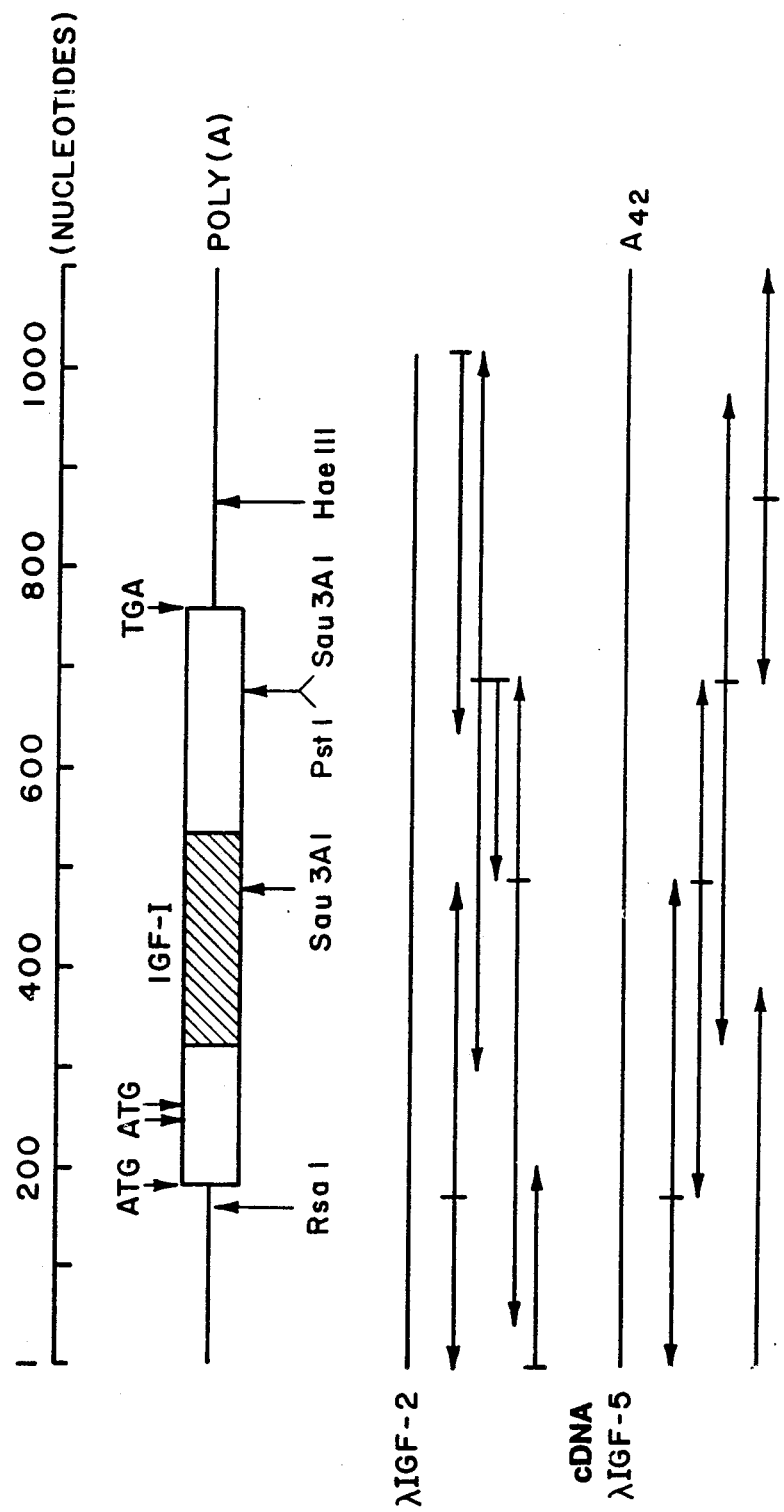
FIG. 1 depicts a map of a human IGF-1B cDNA clone. The horizontal directional arrows denote the approach to DNA sequencing of the cDNA: the open box denotes the 585 base open reading frame and wherein the cross hatched box denotes the DNA sequence encoding the mature human IGF-I peptide; the thin lines denote the 5' and 3' untranslated regions of the 1136 nucleotide cDNA. Below the map of the human IGF-1B cDNA are representative cDNA clones denoted λIGF-2 and λIGF-5. The "A$_{42}$" on the λIGF-5 clone denotes a poly A coding sequence consisting of 42 adenosine (A) bases.

The bottom line represents IGF-1A. The terminal (5' and 3') nucleotides are denoted by an "X".

FIG. 6 depicts the amino acid sequence of the ppIGF-1B protein.

DETAILED DESCRIPTION OF THE INVENTION

As used herein, the symbols representing amino acids (e.g. Ala for alanine) and nucleotides (G,C,A,T) are those conventionally employed. See Lehninger (1976).

As used herein, "gene" refers to a region of chromosomal DNA which region contains DNA sequences encoding a given protein. Typically, eucaryotic genes contain both introns and exons. The term "exon" refers to those gene (e.g. DNA) sequences which are transcribed into RNA. A given exon can, therefore, comprise both protein encoding (coding) and non-coding DNA sequences wherein both the coding and non-coding DNA sequences are transcribed into RNA but only the coding sequences are translated into protein. The term "intron" refers to a DNA sequence present in a given gene which is neither transcribed nor translated and is generally found between exons (hence the name "intron").

The term "essentially pure," when used herein, to describe a protein, peptide, nucleic acid (DNA or RNA) sequence, gene and/or molecule, means substantially free from proteins, peptides, nucleic acid sequences, genes and/or molecules with which the described protein, peptide, nucleic acid sequence, gene and/or molecule is associated in its natural (e.g. in vivo) state.

The term "synthetic" when used herein to describe a protein or peptide means a protein or peptide produced by a technique (e.g. chemical or enzymatic synthesis or recombinant DNA expression) other than its natural production in an animal. Thus, as produced, "synthetic proteins or peptides" are typically essentially pure (e.g. free from proteins or peptides of natural origin). Similarly, with reference to DNA sequences or molecules, the term "synthetic" means that such DNA sequences or molecules have been made by any technique other than their natural replication in vivo. Thus, utilizing the nucleotide sequences described herein, any DNA sequence of this invention can be prepared by various "synthetic" techniques known to those skilled in the art such as, but not limited to, automated DNA synthesizing equipment, other chemical synthesis procedures, enzymatic isolation, cDNA synthesis or cloning techniques.

The term "carboxyl-terminal extension peptide" or, alternatively, "extension peptide" as used herein means a peptide encoded in the DNA sequences down stream (3') to the DNA sequence encoding mature IGF-I. For example, one extension peptide of the present invention has the following amino acid sequence:

NH₂—Arg—Ser—Val—Arg—Ala—Gln—Arg—
His—Thr—Asp—Met—Pro—Lys—Thr—Gln—
Lys—Tyr—Gln—Pro—Pro—Ser—Thr—Asn—
Lys—Asn—Thr—Lys—Ser—Gln—Arg—Arg—
Lys—Gly—Trp—Pro—Lys—Thr—His—Pro—
Gly—Gly—Glu—Gln—Lys—Glu—Gly—Thr—
Glu—Ala—Ser—Leu—Gln—Ile—Arg—Gly—
Lys—Lys—Lys—Glu—Gln—Arg—Arg—Glu—
Ile—Gly—Ser—Arg—Asn—Ala—Glu—Cys—
Arg—Gly—Lys—Lys—Gly—Lys—COOH

A second extension peptide consists of the underlined amino acids in the above sequence. This second extension peptide is encoded in the novel IGF-I exon 4 of the present invention. These extension peptides are believed to possess and/or confer, to proteins encoded in the IGF-I gene, an enhanced biological activity.

It is also understood by those of skill in the art, that references to the proteins of this invention by their respective amino acid sequences embraces various amino acid substitutions, additions and/or deletions so long as the activity of the protein is substantially maintained. Similarly, the essentially pure and synthetic DNA sequences and genes identified by the present invention are understood to embrace various nucleotide sequence variations such as nucleotide deletions, substitutions, inversions, additions, allelic variations and/or functional equivalents for expression of protein(s) encoded therein so long as the activity of the protein(s) encoded therein is substantially maintained. Such amino acid and nucleotide sequence variations are well known to those of skill in the art and can be created by such conventional techniques as de novo chemical synthesis, enzymatic manipulations and recombinant DNA techniques. It is anticipated, for example, that alterations of the specific DNA sequences and/or genes of the present invention can be made in accordance with known genetic code degeneracies to meet the codon and/or expression preferences of specific host cells or organisms employed to synthesize protein(s) of the present invention.

DNA of the Invention

In one embodiment of the present invention, a novel IGF-I specific cDNA, designated herein as IGF-1B cDNA, was identified and isolated. The nucleotide sequence of this IGF-1B cDNA was determined to be as shown in FIG. 2. Further DNA sequence analysis of the IGF-1B cDNA revealed a 585 nucleotide open reading frame (nucleotides 183 to 767, FIG. 2) which encodes a novel 195 amino acid preproinsulin-like growth factor-1 protein designated herein as ppIGF-1B. The amino acid sequence of the novel ppIGF-1B is as shown in FIG. 6. As described more fully below and shown in FIG. 5, a comparison between the IGF-1B cDNA and the ppIGF-I cDNA published by Jansen et al. (1983) revealed the IGF-1B cDNA to be a novel and distinct synthetic DNA sequence encoding a novel and distinct ppIGF-I protein (e.g. ppIGF-1B). Specifically, while the IGF-1B cDNA sequence was determined to be essentially homologous to the sequence of Jansen et al. (1983) for the first 402 nucleotides, the nucleotide sequence then sharply diverges. The Jansen et al. (1983) and IGF-1B cDNAs thus give rise (e.g. encode) two different and distinct ppIGF-I proteins differing in both size (195 amino acids for IGF-1B versus 153 amino acids) and carboxyl-terminal extension peptide composition, the significance of which is discussed more fully below.

The novel IGF-1B cDNA was demonstrated to be useful in producing ppIGF-1B in vitro and is anticipated to provide a synthetic DNA sequence useful for production of ppIGF-1B, or any portion thereof, in suitable host cells (i.e. bacterial, yeast, mammalian or plant) by conventional recombinant DNA techniques and genetic engineering. It is also anticipated that in selected mammalian cells, the synthetic IGF-1B DNA sequence may be useful in producing mature IGF-I as a result of cellular or post-production processing of the ppIGF-1B to mature IGF-I.

Having now provided the DNA sequence of the IGF-1B cDNA (see FIG. 2), synthetic DNA molecules comprising said sequence can now be created by such conventional means as automated DNA synthesis.

In one embodiment of the present invention, the IGF-1B cDNA was isolated from a cDNA library constructed from human liver messenger RNA (mRNA). The cDNA library was constructed and screened for clones containing IGF-I cDNA in accordance with the methods described by Kwok et al. (1985) and Gubler and Hoffman (1983). Although the liver is believed to be the major site of IGF production, many other tissues, for example fetal tissues and fibroblasts are believed to synthesize IGF's as well. Thus, such other tissues may alternatively be employed to construct a human cDNA library.

In one preferred embodiment of the present invention, an oligonucleotide probe corresponding to a mature IGF-I coding sequence was employed to screen the human cDNA library for the presence analysis of clones containing IGF-I specific cDNA sequences. Specifically, the probe comprised a 42 nucleotide molecule (42 mer) corresponding to the DNA sequence encoding amino acids 10 through 23 (see amino acids 58–70 in FIG. 6) of mature, human IGF-I. Such a probe can be used to isolate genomic, cDNA and/or RNA sequences encoding all or a portion of mature IGF-I. Any other region of the mature IGF-I DNA coding sequence may alternatively be employed. Additionally, the length (e.g. number of nucleotides) of such an oligonucleotide probe may vary depending upon the stringency of the hybridization conditions employed. Typically, such an oligonucleotide probe should consist of at least 13 or 14 nucleotides sharing homology with the DNA or RNA sequence(s) sought to be identified.

The screening of a cDNA library with a probe directed to mature IGF-I allows for the identification of potentially all IGF-I messenger RNAs (mRNAs) actively expressed in the tissue from which the cDNA library was constructed. The translation of such mRNAs can include, but are not limited to mature IGF-I, IGF-I precursors which contain at least a portion of the mature IGF-I protein, and any other proteins containing at least a portion of the mature IGF-I protein at the mRNA level of said proteins' biosynthesis. Although, the preferred embodiment employed a cDNA analysis of IGF-I gene products, one may alternatively screen cellular mRNA by Northern Blot analysis in accordance with methodologies known to those skilled in the art to identify IGF-I—specific mRNAs. See Thomas, P. S. (1980).

As described more fully below, clones containing IGF-I specific DNA sequences were then isolated and cleaved with various restriction endonucleases to determine both the size and regions of the IGF-I specific cDNA inserts contained therein. Any restriction enzymes may be employed, see Maniatis et al. (1982). By these means, IGF-I cDNA inserts ranging from about 800 to about 1150 nucleotide pairs in size were identified and isolated. The subsequent restriction mapping of these DNA inserts, unexpectedly revealed that the isolated inserts were of two types, designated herein as IGF-1A cDNA (IGF-1A) and IGF-1B cDNA (IGF-1B), respectively. This discovery of a novel ppIGF-I protein coding sequence is significant as it now provides a means for identifying and isolating novel IGF-I gene sequences, production of a synthetic, essentially pure, novel ppIGF-I protein and means by which mature IGF-I biosynthesis can be studied and possibly manipulated to achieve desirable biological activities and/or effects.

DNA sequence analysis of these two cDNAs was then performed and the respective sequences compared as shown in FIG. 5. As previously discussed, the IGF-1B cDNA is a novel and distinct, synthetic IGF-I DNA sequence which encodes a ppIGF-I protein, referred to as ppIGF-1B. The IGF-1A cDNA was determined to be equivalent to the cDNA sequence isolated by Jansen et al. (1983). Significantly, both the IGF-I cDNA's (-1A and -1B) isolated by the methods of the present invention contained additional 5'-end sequences which now enable an accurate determination of all possible translational starts of the precursor protein(s) (ppIGF-I) encoded therein.

Specifically, as shown in FIG. 2, four possible translation start-signal codons (ATG's), in-frame with the DNA sequence encoding mature IGF-I, were identified. The first ATG codon begins at nucleotide 84, the second at 183, the third at 252 and the fourth at 261. As shown in FIG. 2, the novel 5' IGF-1B cDNA sequences of the present invention also indicate the presence of two in-frame translation termination codons (denoted ### and ***) upstream from (5' to) and in-frame with the second ATG codon beginning at nucleotide 183 thereby suggesting that nucleotides 183 to 185 represent the first operable translation start-signal codon (ATG) for the ppIGF-I protein(s). Indeed, as shown more fully in the examples below, nucleotides 183 to 185 do, in fact, constitute an operable translation start-signal codon (ATG) for the ppIGF-I proteins encoded in both the IGF-1A and -1B synthetic DNA sequences.

This finding is significant as both definitive translation start-signal codons and translation termination codons should be identified within a given gene or synthetic DNA sequence before the amino acid sequence of a given protein or proteins encoded therein may be deduced and/or subsequently produced therefrom. The IGF-I gene and synthetic DNA sequences provided by the present invention represent the first such delineation of the operable translation start-signal codons for both the newly discovered IGF-1B encoded ppIGF-I protein (ppIGF-1B) and for the IGF-I precursor protein proposed by Jansen et al. (1983). Furthermore, the identification of the translational start for the ppIGF-I protein(s) now enables quantitative and qualitative production of synthetic ppIGF-I protein(s) by such conventional means as chemical, enzymatic and/or recombinant DNA methodologies.

Indeed, as described in the examples below, the ppIGF-I proteins of the present invention can be effectively produced by causing expression of the ppIGF-I cDNAs, identified and isolated herein, in an in vitro cell lysate expression system. Alternatively, ppIGF-1A and -1B proteins and/or fragments thereof can be produced by recombinant DNA (rDNA) techniques. Recombinant DNA production methodologies would involve the cloning, by conventional techniques, of at least the protein coding sequences (e.g. at least nucleotides 183 to about 767, FIG. 2, for IGF-1B) into cellular (bacterial, yeast, mammalian and/or plant) expression vectors, available to those of skill in the art, and subsequent production (e.g. expression of the ppIGF-I DNA coding sequences) of the ppIGF-I protein in the selected host cell. The proteins so produced can then be isolated by conventional techniques. By these and other conventional means, such as, but not limited to chemical synthesis, the DNA sequence information and synthetic DNA sequences containing all or part of the IGF-1A and IGF-1B cDNA's, can be employed to produce essentially pure mature IGF-I, ppIGF-I (e.g. ppIGF-1B) and/or an extension peptide.

Additionally, the DNA sequences and genes of the present invention enable those skilled in the art to more effectively study and/or manipulate mature IGF-I biosynthesis and biological regulation. Furthermore, all or portions of the IGF-I gene or DNA sequences of the present invention can be employed to identify equivalent DNA molecules, RNA molecules, gene(s) and/or allelic variations thereof in human and other species (i.e. bovine, porcine and/or avian) wherein sufficient homology in such DNA and/or RNA sequences exists. Indeed, an example of such RNA molecules embraced by the present invention include the 1.7, 3.7 and 6.3 kb (kilobase) polyadenylated IGF-I RNAs identified by hybridization with the IGF-1B cDNA and/or a synthetic DNA encoding the novel extension peptide. The degree of homology necessary to identify such DNA and/or RNA sequences or molecules is well known to those skilled in the art and may, for example, vary depending upon the stringency of the hybridization conditions employed and/or relative sizes of the genes or nucleic acid sequences and probe employed.

With regard to allelic variations of the gene and DNA sequences provided herein, the (IGF-1A) cDNA of Jansen et al. (1983) was determined to maintain an identity (e.g. precise homology) with the novel IGF-1B for 413 nucleotides, except for one nucleotide difference in the Jansen et al. (1983) cDNA sequence, that difference being a conservative third position change in a glycine codon (nucleotide 452 of the IGF-1B sequence). Such position changes in a given codon may result from and/or exemplify allelic variation. Such allelic variations as they may occur in the IGF-1B DNA sequences of the present invention, are considered to represent equivalents of the IGF-I gene and DNA sequences provided herein.

As shown in FIG. 5, after identity for 459 nucleotides, the IGF-1A and IGF-1B DNA's then diverge. Specifically, when analyzed in terms of protein sequence, shown in FIG. 2, the point of divergence follows a lysine residue 16 amino acids after the mature IGF-I region. As described more fully below, the point of divergence corresponds to an exon-intron junction present in the IGF-I gene structure shown in FIG. 3. The IGF-1A cDNA sequence encodes an additional 19 amino acids past the point of the IGF-1A and -1B divergence and thereby encodes a ppIGF-I protein which may be as long as 153 amino acids in length, hereinafter referred to as ppIGF-1A. The IGF-1B cDNA sequence contains an additional 61 amino acids past the point of the IGF-1A and -1B divergence and thereby encodes a ppIGF-I protein which may be as large as about 195 amino acids in length, referred to as ppIGF-1B. The two carboxyl-terminal extensions consisting essentially of the 19 amino acids of IGF-1A and 61 amino acids of IGF-1B, respectively, show no amino acid homology with each other. Additionally, neither carboxyl-terminal extension peptide showed homology with any other protein in the National Biomedical Research Foundation Protein Sequence Data Bank. Dayhoff et al. (1983) and Wilbur and Lipman (1983). These differences coupled to the discovered existence of two distinct ppIGF-I cDNAs verified by the subsequent identification in vivo of corresponding mRNA molecules (see examples, below) confirms that the synthetic ppIGF-1B DNA sequence provided in the present invention represents a novel ppIGF-1 cDNA encoding a novel and distinct ppIGF-I protein (ppIGF-1B) and extension peptide(s).

In another important embodiment of the present invention, a novel human IGF-I gene was identified and isolated. Unlike the gene identified by Bell et al. (1985), the IGF-I gene of this invention contains 5 exons and encodes at least two ppIGF-I proteins. The gene structure and DNA sequence of the novel IGF-I gene is shown in FIGS. 3 and 4, respectively. While exons 1, 2, 3 and 5 as shown in FIG. 3 were structurally identified by Bell et al. (1985), the complete DNA sequences of these exons were not provided. These sequences are essential for determining the number and amino acid composition(s) of possible ppIGF-I protein(s) encoded in the IGF-I gene. Furthermore, the sequence information is essential for subsequent employment of the gene or portions thereof (e.g. specific exons or intron-exon combinations) in in vitro or in vivo protein production systems.

For purposes of synthesizing ppIGF-I proteins, IGF-I gene related proteins and mature IGF-I proteins in, for example, mammalian systems, it may be desirable to employ an essentially pure IGF-I gene, or portions (e.g. exons) thereof. Specifically, it may be desirable to employ IGF-I specific DNA sequences comprising intron and exon regions. Alternatively, employment of essentially intron-free DNA sequences derived from the IGF-I gene provided herein may be desirably employed to produce ppIGF-I proteins or extension peptides. For these reasons and for purpose of positioning the novel DNA sequences of the present invention within the IGF-I gene sequence, we isolated and cloned IGF-I gene sequences.

In one preferred embodiment of the present invention, two genomic libraries were screened for IGF-I gene inserts employing IGF-1A and -1B cDNA's or fragments thereof. As described more fully below and shown in FIGS. 3 and 4, we identified five exons whereas only 4 exons had previously been reported. See Bell et al. (1985). The newly discovered exon 4 (see FIGS. 3 and 4) was determined to encode a carboxyl-terminal extension of ppIGF-1B whereas exon 5 encodes a carboxyl-terminal extension of ppIGF-1A.

Exon 1 encodes at least 21 amino acids which may comprise a leader peptide enabling secretion of IGF-I. IGF-I is known to be secreted by the cells producing it hence the term "preproinsulin-like growth factor-I" (ppIGF-I) to denote an IGF-I precursor protein. Exon 2 is about 157 nucleotides in length and encodes 52 amino acids and is identical in DNA sequence to an IGF-I exon reported by Ullrich et al. (1984). The initial 27 amino acid residues encoded in exon 2 precede the start of the mature IGF-I B domain and contain two methionine residues which may serve as additional translation start signals. Exon 2 also encodes the beginning 25 amino acids of the B domain of mature IGF-I. Codon 26 was found to be interrupted by a large intron of at least 21 kb. The remainder of the genetic information coding for the mature IGF-I protein resides in exon 3. Specifically, exon 3 contains 11 nucleotides encoding the rest of the B domain, 12 codons encoding the C domain, 21 codons encoding the A domain and 8 codons encoding the D domain. In addition, exon 3 codes for 16 additional amino acids which may represent a newly described E domain and/or a portion of the carboxyl-terminal extension of pIGF-1A and pIGF-1B.

Thus, the "carboxyl-terminal extension proteins" or "extension peptides" of the present invention can comprise a combination of the last 16 amino acids encoded in exon 3 (e.g. NH$_2$—Arg Ser Val Arg Ala Gln Arg His Thr Asp Met Pro Lys Thr Gln Lys—COOH) and the peptide encoded in exon 4.

Exons 4 and 5 were found to each encode distinct extension peptides, translation termination codons, 3' nontranslated regions, poly A addition (e.g. adenylation) signals and sites. Exon 4, located 1.5 kb 3' to exon 3, consists of 515 nucleotides and comprises the 3'-end (e.g. carboxyl-terminus) of the IGF-1B coding sequence. The extension peptide encoded in exon 4 comprises a highly basic 61 amino acid peptide with several dibasic an tribasic residues. Based upon analogies with other biosynthetic pathways employing precursor protein intermediates (e.g. conversion of proinsulin to insulin), these dibasic and tribasic residues may provide for the enzymatic processing of the ppIGF-I protein(s) encoded in the gene or genes of the present invention into, for example, a mature IGF-I protein. Additionally or alternatively these residues may facilitate binding to such negatively charged macromolecules as DNA. Following the TGA termination codon in exon 4, are 329 bases of 3' nontranslated DNA. Exon 5, located 17 kb downstream (3') from exon 3 is 344 bases long, encodes the 3'-end of the IGF-1A coding sequence and contains a TAG translation termination codon and 284 bases of 3' nontranslated DNA. Additionally, all intron-exon borders contain consensus RNA splicing sequences indicating that any combination of exons may exist within a mRNA molecule and, hence, be translated into an IGF-I gene related protein.

The genes and DNA sequences provided herein now allow the production, in vitro, by such techniques as recombinant DNA and chemical synthesis, and the detection, in vivo, of proteins comprising a single exon encoded protein and/or any combination of exon encoded proteins. Such proteins are believed to be biologically active and, specifically, to possess IGF-I-like activity. As such, the attendant biological activities maybe ascertained by those skilled in the art employing in vitro and/or in vivo assays, see Daughaday (1977); Clemmons and Van Wyk (1981a); van Buul-Offers and Van de Brande (1980); Schoenle et al. (1982); and Hylka et al. (1985).

Furthermore, the isolation, restriction map and determination of the IGF-I gene structure and sequence is significant as it now provides an opportunity to localize DNA polymorphisms detected by, for example, chromosomal restriction endonuclease analysis. Indeed, we have localized the site polymorphisms for restriction endonucleases Hind III and Pvu II to be linked to one another and to map to exon 5 of the genomic IGF-I gene. Such polymorphisms are useful in establishing familial genetic linkages and have been employed diagnostically for various diseases. Additionally, such IGF-I gene polymorphisms may be employed diagnostically for growth-affected conditions. Furthermore, such polymorphisms are considered to constitute equivalents of the gene sequences provided herein.

The present invention further contemplates that the essentially pure IGF-I gene of the present invention or portions (e.g. exons) thereof may now be employed to generate, de novo, and/or amplify, in vivo, IGF-I gene related proteins including but not limited to ppIGF-I proteins, mature IGF-I proteins, variants thereof and/or biosynthetic intermediates thereof.

The Proteins

In one embodiment, the present invention is directed to a novel ppIGF-I protein (ppIGF-1B) having an amino acid sequence as shown in FIG. 6. In another important embodiment, the present invention is directed to novel extension peptides exemplified by a peptide having the amino acid sequence as shown for the extension peptide of mature human IGF-I depicted both above and in claim 4. Based upon the sequences provided herein, these proteins and equivalents thereof can now be made by such conventional means as chemical synthesis, in vitro enzymatic synthesis, rDNA techniques and/or isolation from human tissue.

It is anticipated that production of the proteins or peptides of this invention by rDNA and/or chemical synthesis may result in minor alterations in amino acid composition. For example, production in bacteria may result in addition of a methionine at the amino (NH$_2$)-terminus and chemical synthesis may result in variations of the carboxy (—COOH) terminus such that any of the radicals —COOR, —CRO, —CONHNR$_1$, —ConR$_1$R$_2$ or —CH$_2$OR (R$_1$ and R$_2$ being independently lower alkyl or hydrogen) may be found. Such essentially pure and/or synthetic proteins are considered within the scope those of the present invention.

Furthermore, the novel DNA sequences and genes provided by the present invention now enable those skilled in the art to identify, isolate and/or produce ppIGF-I proteins and/or biologically active fragments thereof including, but not limited to, mature IGF-I and extension peptides. The biological activity of these proteins, may include, but is not limited to, the growth promoting activit(ies) of mature IGF-I and can, therefore, be ascertained in accordance with the in vitro and in vivo assays known to those skilled in the art.

Specifically, IGF-I has been shown to stimulate cell proliferation, skeletal growth, weight gain and mammary gland growth, the latter being a prerequisite for enhanced milk production. It is anticipated that the novel ppIGF-1B protein described herein shares all or some of such growth promoting activities and can exhibit enhanced activity in selected tissue.

It is also anticipated that biologically active fragments of the proteins of this invention can be made by conventional means. These fragments are hereinafter sometimes referred to as "IGF-I gene related proteins" and are understood to comprise proteins wherein at least a portion of said protein(s) is encoded in the gene and/or synthetic DNA sequences of the present invention and/or allelic variations thereof.

In one approach, the amino acid sequences of the ppIGF-I (e.g. ppIGF-1A and ppIGF-1B) proteins and extension peptides thereof were deduced from the DNA sequences of their respective cDNAs and from the novel IGF-I gene provided by the present invention. For example, the ppIGF-1B protein was determined to have the amino acid sequence as given in FIG. 6.

In another approach, the ppIGF-I proteins were identified by employing in vitro systems which provided for expression of the IGF-1A and -1B cDNAs. The term "expression" as used herein when referring to a gene or synthetic DNA sequence means transcription of a given gene or DNA sequence into mRNA followed by translation of the mRNA into protein. The proteins so produced can thereafter be isolated by such conventional techniques as polyacrylamide gel electrophoresis, affinity chromatography, ion-exchange, reverse phase HPLC, immuno-precipitation or any other conventional fractionation technique and then sequenced. By these methods, it was demonstrated that a 195 amino acid ppIGF-1B protein and a 153 amino acid ppIGF-1A protein can be produced in vitro, that these proteins corresponded to their respective amino acid sequences deduced from their respective cDNA sequences identified herein and that the first in-frame methionine codon [e.g. base pairs 183–185 for IGF-1B (see FIG.2)] is the major translation start-signal codon for both ppIGF-I proteins.

In order to confirm that the proteins (e.g. ppIGF-1A and ppIGF-1B) encoded in the synthetic IGF-1A and-1B DNA sequences and/or the carboxyl-terminal extensions thereof are produced as distinct and separate peptides and/or as part of separate and distinct proteins in vivo, we did the following. Radiolabeled complete IGF-1A cDNA or complete IGF-1B cDNA and radiolabeled DNA's corresponding to the coding sequences contained in either exon 4 or exon 5, were individually hybridized to RNA transcripts (mRNA) produced in human liver.

By these means, we identified polyadenylated RNA molecules ranging from about 900 to about 1350 nucleotides in length which hybridized to all of the aforementioned probes. These results confirm the active transcription of DNA encoding both the IGF-1A and -1B DNA sequences in vivo. Furthermore, we identified three additional polyadenylated RNAs (mRNAs) approximately 1.7, 3.7 and 6.3 kilobases (kb), respectively, in length. While applicants do not wish to be bound by the following theory of mechanism, we believe that these larger mRNAs represent forms of ppIGF-I precursor mRNAs or mRNAs encoding IGF-I gene related proteins (e.g. proteins consisting essentially of the sequence of essentially pure ppIGF-I and/or an essentially pure extension peptide). Additionally, our discovery that the human IGF-I gene of the present invention elaborates multiple proteins represents a means by which IGF-I biosynthesis and/or maturation may be regulated and/or a means by which IGF-I gene related proteins may be regulated and/or synthesized. Specifically, as IGF-I is required primarily to support linear growth, the levels of gene expression may vary during growth and development and/or may vary in different tissues depending upon the growth requirements of said tissue(s). The ppIGF-I proteins may provide a point of regulation for mature IGF-I production and/or IGF-I gene related protein production during these growth stages and/or in a tissue specific manner.

The identification and isolation of the ppIGF-I cDNAs and corresponding mRNA synthesized in vivo suggest that the ppIGF-I proteins of the present invention are made in vivo. Although yields are expected to be low, relative to commercially desirable yields, it is anticipated that based upon the DNA and amino acid sequences provided herein, essentially pure ppIGF-I proteins may be isolated from tissue (i.e. fibroblasts, blood, liver, etc.) and/or cells therefrom. Such essentially pure proteins are considered to be part of the present invention.

The recent identification of a rat IGF-II protein containing an E domain and isolation of an active free peptide representing the E domain in rat serum, Zumstein et al. (1985) and Hylka et al. (1985), suggests that a family of IGF gene related biologically active peptides or proteins may be made in vivo. Such proteins would include but are not limited to the novel IGF-1B carboxyl-terminal extension peptide disclosed herein. It is also anticipated that proteins consisting of various combinations of IGF-I gene exons may be included in such a family of IGF gene related proteins. For example, the carboxyl-terminal extension peptides of pIGF-1A and/or 1B may serve specific tissue-limited, biological functions. The functions of the alternatively expressed carboxyl-terminal peptides may be examined by those skilled in the art by employing, for example, synthetic peptides and antibodies thereto. Alternatively, RNA splicing may provide a point of regulation for IGF-I gene expression as has been suggested for other genes, Rosenfeld et al. (1983), in which different combinations of exons function in different tissues. Such possible exon combinations are considered to be embraced by the present invention.

The present invention also contemplates that the genes and DNA sequences provided herein may be employed to generate and/or aid in the isolation of said IGF-I gene related proteins. While the present invention describes a specific ppIGF-1B amino acid sequence encoded in such genes and DNA sequences, it is anticipated that alternative open reading frames and thus alternative protein (e.g. amino acid sequences) may be encoded in the gene and DNA sequences provided herein. Such proteins are herein considered to be among the IGF-I gene related proteins provided for by the novel genes and DNA sequences provided herein.

As previously discussed, it is believed that the novel ppIGF-I and extension peptides of the present invention are useful for administration to animals for promoting growth, increasing milk production and/or the lean-to-fat ratio or muscle content in animals. For purposes of such uses, one or more proteins or peptides of this invention (or non-toxic salts thereof) can be combined with a non-toxic, physiologically acceptable carrier (liquid or solid) to form a composition which can be administered to animals by any suitable technique, e.g. intravenously, subcutaneously, intramuscularly, intranasally, or orally in a form that protects the proteins or peptides from degradation in the digestive tract. Such compositions can be administered to the animal by injection, infusion or implantation, preferably in a medium (e.g. dispersion in oil or a polymer) which facilitates delivery of the peptide to target cells of the animal at a desired rate. One such method for administration to an animal (e.g. pregnant cows and heifers) is intramammary infusion of the protein or peptide in a vehicle suitable for achieving adequate dispersion in mammary tissue as taught in more detail in copending U.S. Pat. application, Ser. No. 837,477, filed Mar. 7, 1986. The disclosure of said application is incorporated herein by reference. The proportions of carrier and biologically active peptide in such compositions can be any that facilitate the desired effects in animals. Preferred proportions can be readily determined by those skilled in the art.

The required dosage will vary with the particular result sought and duration of desired treatment. An effective dose of the ppIGF-1B protein and/or extension peptide(s) is from about 60 micrograms ($\mu$g) to about 6 milligrams (mg) per kilogram (Kg) of animal body weight administered daily for a treatment period of from about one to about three weeks. A more preferred dose is from about 400 $\mu$g to about 800 $\mu$g per Kg per day. As used herein, a therapeutically effective concentration is defined as a concentration of the particular protein or peptide which provides a satisfactory stimulation in the desired cellular growth and/or functionality. The most preferred amount or dosage most effective for achieving a desired result (e.g. increased milk production) can be determined by routine experimentation. The preferred dosage may depend on such variables as the size, general health and nutritional status of the specific animal.

Bioactive peptides of this invention can be used in an essentially pure form, i.e., free from other proteins or peptides (of whatever origin) having a significant effect on the bioactivity of the proteins or peptide(s) of this invention. This is not essential, however, as in many utilities proteins or peptides of this invention can be used satisfactorily (in many cases, even advantageously) in mixtures or other combinations with different proteins or peptides, e.g. other animal growth factors such as bovine (or other animal) IGF-I, EGF or TGF-α (alpha-transforming growth factor).

The following examples illustrate preferred embodiments of the present invention and are not intended to limit the invention's scope in any way. While this invention has been described in terms of its preferred embodiments, various modifications and variants thereof shall be apparent to one skilled in the art from reading this application.

All enzymes including restriction enconucleases, $T_4$ DNA ligase, $T_4$ polynucleotide kinase, DNA polymerase, ribonuclease A, DNA modifying enzymes, wheat germ lysates, rabbit reticulocyte lysates, unlabelled amino acids and proteinase K were purchased from New England Biolabs (Beverly, Mass.) and Bethesda Research Laboratories (BRL) (Gaithersburg, Md.) and used in accordance with manufacturer's specifications. Nitrocellulose filters were obtained from Scheicher and Schuell (Keene, N.H.) and Millipore (Bedford, Mass.). Radionuclides and radiolabelled amino acids were purchased from New England Nuclear (Boston, Mass.) and Amersham (Arlington Heights, Ill.). Deoxyribonucleoside triphosphate, ribonucleoside triphosphates and dideoxyribonucleoside triphosphates were purchased from Pharmacia-PL Biochemicals (Piscataway, N.J.).

A 42 base oligonucleotide corresponding to the DNA sequence encoding amino acids 10 to 23 of mature human IGF-I (Jansen et al. 1983 and Ullrich et al. 1984) was synthesized in the Department of Biological Sciences, Monsanto Company (St. Louis, Mo.) employing an Applied Biosystems DNA Synthesizer in accordance with the procedure set forth by the manufacturer. Applied Biosystems, Inc. (Foster City, Calif.). The sequence of the 42 mer was as follows:

5'—AAAGCCCCTGTCTCCACACAC-GAACTGAAGAGCATCCACCAG—3'

The 42 mer was labeled at the 5' end by using gamma $^{32}P$ adenosine triphosphate and $T_4$ polynucleotide kinase in accordance with the procedure set forth by Maniatis et al. (1982) to achieve a specific activity of about $10^7$ dpm per picomole. The radiolabeled 42 mer was then employed to screen for IGF-I containing DNA sequences in a human liver cDNA library made in accordance with the procedures set forth by Kwok, S. C. M. et al. (1985) and Gubler and Hoffman (1983). The human liver cDNA library in lambda gtII was obtained from Drs. S. L. C. Woo and T. Chandra (Baylor University School of Medicine, Houston, Tex.). Lambda gtII may also be obtained from the American Type Culture Collection (ATCC) (Rockville, Md.) under ATCC accession number 37194 and a human cDNA liver library prepared therein in accordance with the procedure described by Kwok, S. C. M. et al. (1985). *E. coli* K12 strain Y1088 may be obtained from ATCC under ATCC accession number 37195. The plasmids pGEM1 and pGEM2 were obtained from Promega Biotech (Madison, Wis.).

EXAMPLE 1

The following example demonstrates the isolation of IGF-1A and IGF-1B cDNA's from a human liver cDNA library.

Briefly, the human liver cDNA library in lambda gt11 was screened as follows. Lambda gt11 was plated on *E. coli* K12 strain Y1088 in accordance with the method described by Young and Davis (1983). Duplicate nitrocellulose filters were prepared in accordance with the procedure described by Woo, S. L. C. (1979) and hybridized at 42° C. for about 20 hours using $2 \times 10^6$ dpm of probe per filter in buffer containing $5 \times SSC$ ($1 \times SSC = 150$ mM NaCl, 15 mM Na citrate, pH 7.0), 50 mM Na phosphate, pH 6.8, 40% (v/v) deionized formamide, 50 micrograms/milliliter denatured salmon sperm DNA, $5 \times$ Denhardt solution [0.1% (w/v) ficoll, 0.1% (w/v) bovine albumin, 0.1% (w/v) polyvinyl pyrolidone, Maniatis et al. (1982)]. Following hybridization the filters were washed for 15 minutes at 22° C. and for 15 minutes at 40° C. in a solution containing $0.2 \times SSC$, 0.1% (w/v) sodium dodecyl sulfate (SDS) and were thereafter exposed to Kodak XAR5 film (Eastman Kodak Co., Rochester, N.Y.) using intensifying screens. Positive plaques were rescreened at lower density. Specifically, the primary screening employed about $2.5 \times 10^4$ plaques per 137 millimeter filter and the secondary screening employed about $1-2 \times 10^2$ plaques per 87 millimeter filter. Phage DNA from the positive plaques was then prepared as described by Helms et al. (1985) and mapped by restriction enzyme digestion and gel electrophoresis, Maniatis et al. (1982), and subsequently sequenced.

Approximately $5 \times 10^5$ plaques of the human liver cDNA library were screened as just described with the IGF-I-specific 42 mer probe leading to the isolation of 7 positive plaques with DNA inserts ranging from about 800 to about 1150 nucleotide pairs. By restriction mapping with EcoRI, BamHI and PstI, the cDNA's were found to be of two types. Two of the 7 positive plaques containing inserts of approximately 800 to 850 nucleotide pairs contained internal Bam HI restriction endonuclease sites and were found to correspond to the IGF-I cDNA reported by Jansen et al. (1983). These inserts were designated IGF-1A cDNA. The remaining 5 positive clones shared a restriction endonuclease map that differed from the map of the IGF-1A cDNA. These 5 clones were designated IGF-1B cDNA. The largest two inserts, shown as λIGF-2 and λIGF-5 in FIG. 1 were then selected for DNA sequence analysis.

DNA sequencing was performed by the dideoxy chain terminating method described by Sanger et al. (1977) and Biggin et al. (1983) after subcloning restriction fragments into M13mp18 and M13mp19 bacteriophage as described by Norrander et al. (1983). The sequencing strategy is shown in FIG. 1. The DNA sequences of the two IGF-1B cDNA isolates were determined in their entirety on both strands and across all restriction enzyme sites used as initiation points except for the extreme 3'-end of one clone λIGF-5 (see FIG. 3), which was sequenced three times in only one orientation.

Both isolates gave identical results over shared regions. The DNA sequence and amino acid translation appear in FIG. 2. The aggregate IGF-1B cDNA consists of 1136 nucleotides including 42 deoxyadenosine residues of the poly A tract. The size of the IGF-1B cDNA agrees with the size of the major mRNA (900 to 1350 nucleotides) determined by filter hybridization, described more fully below. The sequence can be divided into three sections: a 5' untranslated region comprising the initial 182 nucleotides; an initiation codon and an open reading frame of about 585 nucleotides (195 codons) followed by an opal (TGA) termination codon; and a 3' untranslated region of about 368 nucleotides ending in a poly A tract.

As shown in FIG. 2, the 585 nucleotide open reading frame begins with the second in phase ATG codon. The first ATG at nucleotides 84 to 86 is followed immediately by an in frame opal terminator. The open reading frame shown in FIG. 2 encodes a ppIGF-I of about 195 amino acids with a molecular weight of about 21,841 daltons assuming that the ATG codon at bases 183 to 185 initiates protein synthesis. The mature IGF-I protein sequence is encoded by nucleotides 327 to 536 denoted by the crosshatched area in FIG. 1 and underlined in FIG. 2. The 70 mature IGF-I codons are followed by a unique and novel carboxyl-terminal extension of 77 amino acids. Although the first 16 amino acids of this carboxyl-terminal extension are identical to the first 16 amino acids of the IGF-1A carboxyl-terminal extension, the remaining 61 amino acids are unique as determined by lack of homology with the IGF-1A carboxyl-terminal extension or with any other protein in the National Biomedical Research Foundation Protein Sequence Data Bank. Dayhoff et al. (1983) and Wilbur and Lipman (1983).

Confirmation of the in vivo expression of two distinct ppIGF-I proteins encoded in the IGF-1A and -1B cDNA's, respectively, was achieved by identifying messenger RNA molecules encoding these proteins. Specifically, liver polyadenylated RNA was isolated from tissue fresh-frozen at $-70°$ C. by extraction with guanidinium thiocyanate in accordance with the procedure described by Chirgwin et al. (1979) and one round of chromatography on oligo dT cellulose are described by Aviv and Leder (1972). The polyadenylated RNA was denatured with glyoxal as described by McMaster and Carmichael (1977), electrophoresed through a 1.25% (w/v) agarose gel and transferred to a nitrocellulose filter by blotting in accordance with the procedure described by Thomas (1980). Complete IGF-1A and 1B cDNA's or DNA's encoding either, the IGF-1A or -1B carboxyl-terminal extensions were all individually labeled with $^{32}$P by nick translation as described by Rigby et al. (1977) to $8+12\times10^8$ dpm per microgram and hybridized to the filters at 42° C. in a solution containing 50% (v/v) formamide, 5×SSC, 50 mM Na phosphate, pH 6.5, 100 micrograms per milliliter denatured salmon sperm DNA, 1×Denhardt solution and 10% (w/v) dextran sulfate. Filters were washed for 15 minutes at 22° C. in buffer containing 0.2×SSC and 0.1% (w/v) SDS, for 30 minutes in two changes of the same buffer at 48° C, and then autoradiographed using intensifying screens for 62 hours at $-70°$ C.

Both IGF-1A and -1B cDNA's hybridized to RNA transcripts in human liver. Hybridization of either the unique carboxy-terminal extension of IGF-1A or -1B cDNA shows a major band of approximately 900 to about 1350 nucleotides. Other larger bands were seen at 1.7, 3.7 and 6.3 kilobases potentially, respectively, processed precursor mRNA's or alternatively other IGF-I gene related mRNA's. Parallel experiments using entire IGF-1A and -1B cDNA's yielded similar results.

EXAMPLE 2

This example demonstrates the isolation and mapping of the human IGF-I genomic gene.

A human genomic library was prepared using a hybrid vector, λMG14, Helms et al. (1985), and size-fractionated human leukocyte DNA, partially digested with MboI as described by Maniatis et al. (1982). Genomic libraries may be prepared as described by Maniatis et al. (1982). Approximately $4\times10^5$ plaques from this library and another derived from human fetal liver, described by Lawn et al. (1978), were screened in accordance with the methods described by Maniatis et al. (1982) using $^{32}$P-labeled IGF-I cDNA's, prepared by nicked translation as described by Rigby et al. (1977), as hybridization probes. DNA from plaque-purified positive isolates, Helms et al. (1985), was mapped using Bam HI, Eco RI and Hind III single and double digestions by hybridization to $^{32}$P IGF-I cDNA's and human Alu probes, prepared as described by Schmid and Jelinek (1982). From 15 genomic clones containing IGF-I exons, 8 were selected for further analysis consisting of restriction endonuclease mapping and Southern blotting. The eight clones selected and genomic DNA regions contained therein are shown in FIG. 3(a) and are marked λIGF- followed by a number.

Figure 3A:
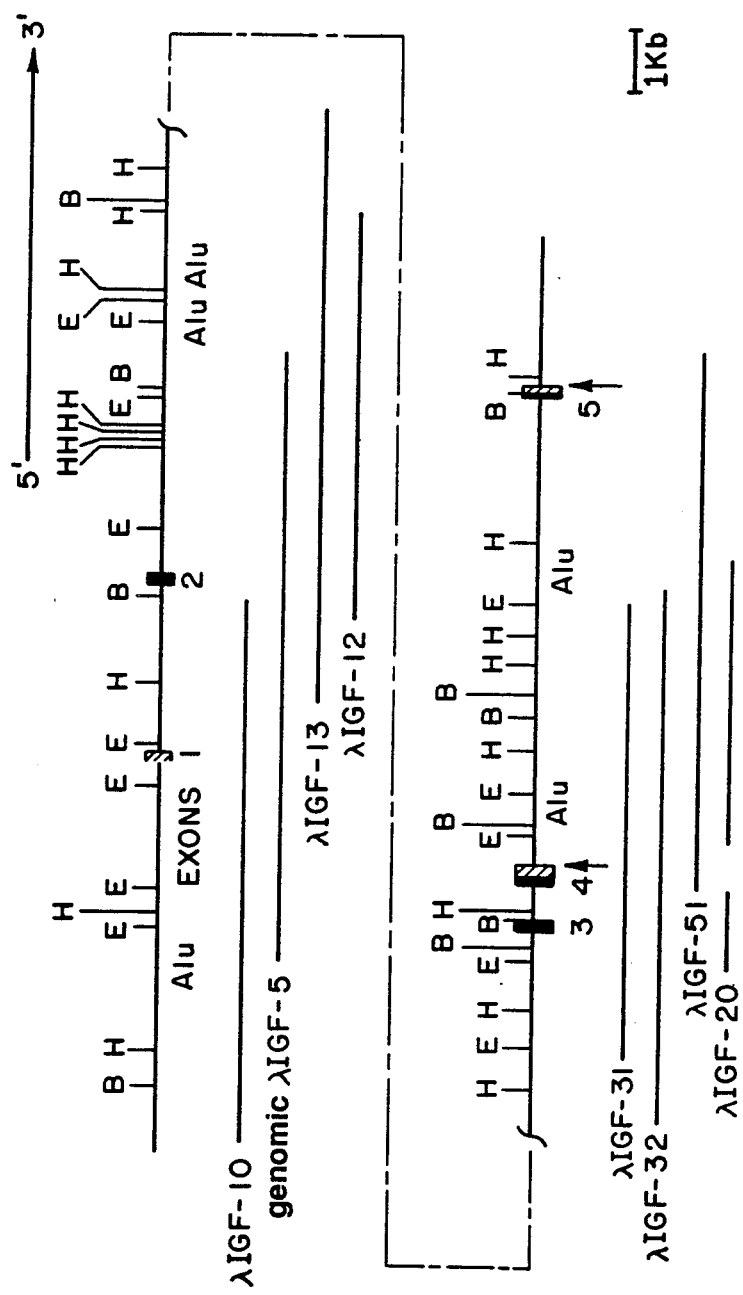
FIG. 3(a) depicts the structure and restriction map of the human IGF-I gene. The 5' to 3'directional arrow indicates the 5' to 3' orientation of the IGF-I gene. The thin lines denote introns and flanking regions; the ∫∫ denotes a region of an intron not isolated by molecular cloning; the solid boxes (1, 2, 3, 4, 5) denote coding regions and the cross-hatched boxes denote non-coding regions of the mRNA; the vertical arrows under exons 4 and 5 denote the polyadenylation sites. The regions marked "Alu" denote hybridization to middle repetitive DNA of the Alu type. Restriction sites are denoted by "B"=BamHI, "E"=EcoRI, "H"=HindIII. Below the restriction map are representative genomic clones. (b) depicts detailed restriction maps of IGF-I exons 1 to 5. The horizontal directional arrows denote DNA sequencing strategy; the boxes denote exons wherein the solid regions denote coding regions and the cross-hatched regions denote noncoding regions of the mRNA. The vertical arrows under exons 4 and 5 denote the polyadenylation sites.
Figure 3B:
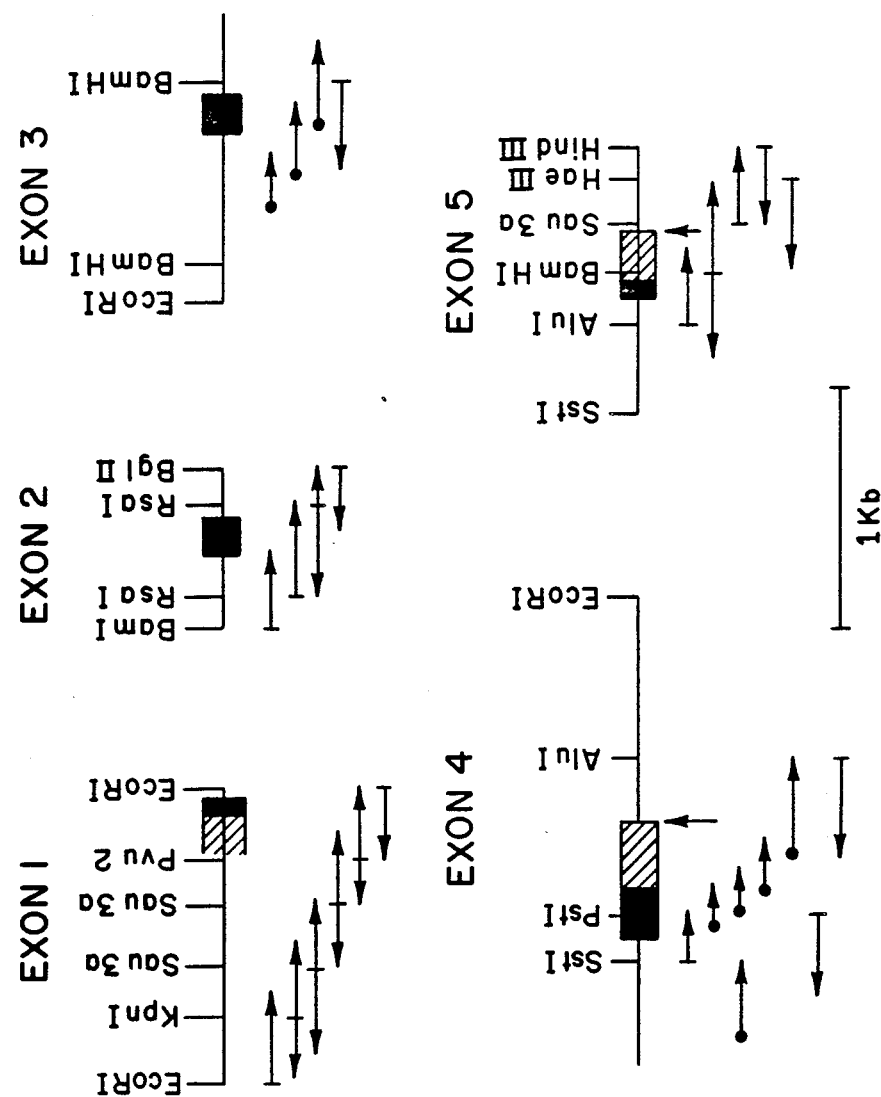

The results of these analyses are summarized in FIG. 3(a) which presents a restriction map of the isolated genomic IGF-I gene. Five regions of the isolated DNA hybridized to the cDNA probes and were designated exons 1–5, shown as the numbered boxes in FIG. 3(a). Exons 1, 2, 3 and 5 comprise IGF-1A mRNA (e.g. DNA encoding ppIGF-1A), and exons 1, 2, 3 and 4 comprise IGF-1B mRNA (e.g. DNA encoding ppIGF-1B). From the beginning of exon 1 to the end of exon 5, the gene extends for more than 45 kilobases (kb). The incompletely characterized DNA region between exons 2 and 3 was determined to represent an intron as that sequence interrupts an asparagine codon in the B domain of mature IGF-I and, thus, cannot contain an additional exon. As shown in FIG. 3(a), within the genomic IGF-I gene are five regions which hybridize strongly to middle repetitive DNA of the Alu type, Schmid and Jelinek (1982). These Alu type sequences map to intervening and flanking DNA sequences. Schmid and Jelinek (1982).

Subclones containing each exon were prepared in pUC18 and pUC19 plasmids in accordance with the procedures described by Norrander et al. (1983) for further restriction mapping, and in M13mp18 and M13mp19 in accordance with the procedures described by Norrander et al. (1983), for DNA sequencing. M13mp18, M13mp19, pUC18 and pUC19 may be obtained from New England Biolabs (Beverly, Mass.). The DNA sequence analysis was performed in accordance with the procedures described by Sanger et al. (1977) and Biggin et al. (1983) using dideoxy chain-terminating inhibitors, $^{35}$S-dATP and both standard and denaturing gel electrophoresis. The DNA sequencing strategy employed is diagramed in FIG. 3(b). Initial DNA sequencing of exons 3 and 4 was obtained after preparing a series of overlapping deletions using Bal 31 exonuclease, described by Poncz et al. (1982), as indicated by the solid circles in the sequencing scheme shown in FIG. 3(b). All other sequence analysis was initiated at specific restriction endonuclease sites as depicted by the short vertical lines in FIG. 3(b). The arrows indicate the extent of sequence determined. Except for 100 nucleotides of the intron preceding exon 2 and a portion of exon 4, all sequences presented in FIG. 4 were verified from both DNA strands, including all restriction endonuclease sites used as initiation points. All exon-intron splice junctions and polyadenylation sites were determined by comparison with IGF-1A and IGF-1B cDNA sequences.

Southern blot analysis was conducted briefly as follows. Ten micrograms of DNA from human leukocytes, Maniatis et al. (1982), were digested with various restriction enzymes Hind III, Pvu II, Eco RI, Bam HI and Bgl II and then electrophoresed through 0.8% (w/v) agarose gels at 20-25 volts in buffer containing 0.089 M Tris-borate, 0.089 M boric acid and 0.001M $Na_2$ EDTA. DNA fragments were transferred to nitrocellulose filters by blotting in accordance with the procedure described by Southern (1975). Prehybridization of the filters, hybridization to radiolabeled IGF-I cDNA probes, prepared as previously described, and posthybridization washes followed the procedure of Wahl et al. (1979). Hybridizing bands were detected by autoradiography.

Southern blot analysis was performed on 18 unrelated adults of normal stature using IGF-1A and IGF-1B cDNA probes and the restriction enzymes listed above. We found the site polymorphisms for Hind III and Pvu II to be linked to one another and to map exclusively near exon 5 of the genomic IGF-I gene.

The complete genomic IGF-I gene sequence is presented In FIG. 4. The region of exon 4 sequenced in one orientation agrees completely with the corresponding cDNA sequence encoding the carboxyl-terminal extension peptide of ppIGF-1B. The DNA sequence of exon 5 agrees completely with the corresponding cDNA sequence encoding the C-terminal extension peptide of ppIGF-1A.

By primer extension analysis using human liver RNA and a $^{32}$P-labeled oligonucleotide, 5'TGAG AGCAATGTCACATTTC3', the 5'-end of the ppIGF-I mRNA was found to extend 583 nucleotides upstream of the prime annealing site at position 1108, FIG. 4. If the 5' untranslated region of the gene does not contain an intron, transcription must begin at position 525 or 526, FIG. 4. If an intron is contained within the 5' untranslated region, transcription would most likely begin further upstream (5') to positions 525 or 526. The IGF-1B cDNA shown in FIG. 2 extends 182 nucleotides 5' to the translation initiation codon and contains several upstream in-phase translation termination codons as denoted in FIG. 4. A region of 42 nucleotides further 5' at positions 199 to 241, FIG. 4, in the sequence contains alternating purine and pyrimidine residues with the potential to form Z DNA, indicative of actively transcribed DNA. Nordheim and Rich (1983).

EXAMPLE 3

This example demonstrates the expression in vitro of IGF-1A and IGF-1B precursor peptides and demonstrates the ability of the first in-frame methionine (ATG) codon to signal the start of ppIGF-I translation.

In the present example, human IGF-1A and IGF-1B cDNAs were separately ligated to the plasmids pGEM1 and pGEM2 to create recombinant plasmids containing an IGF-I cDNA with its 5'- end adjacent to the bacteriophage $T_7$ promoter contained within the pGEM plasmids. Specifically, the IGF-1A cDNA was ligated to a PGEM1 plasmid previously digested with EcoRI. The correct orientation of the IGF-1A cDNA in the recombinant plasmid was verified by restriction endonuclease analysis employing BamHI. Recombinant pGEM2 plasmids containing IGF-1B cDNA were constructed by ligating a RsaI digested IGF-1B cDNA containing an EcoRI linker at its 3'-end to a pGEM2 plasmid previously double digested with EcoRI and HincII. The correct orientation of the IGF-1B cDNA with respect to the $T_7$ promoter in the recombinant plasmid was verified by digest with PstI. After isolation of the recombinant plasmids, designated pGEM1/IGF-1A and pGEM2/IGF-1B, respectively, each plasmid was linearized at the 3' end of the respective IGF-I DNA sequences using enzymes HindIII and EcoRI, respectively. Complementary RNAs, designated IGF-1A cRNA and IGF-1B cRNA, were prepared by transcription in vitro using $T_7$ RNA polymerase (Davanloo et al., 1984), according to the method of Melton et al. (1984). In order to increase the efficiency of subsequence translation, each RNA was co-transcriptionally 'capped', following the procedure of Hart et al. (1985). Capped, full-length IGF-1A and IGF-1B cRNAs were translated in vitro using both wheat germ and rabbit reticulocyte lysates (Pelham and Jackson, 1976), in the presence of $^{35}$S-methionine or $^3$H-leucine and the 19 remaining complement of unlabelled amino acids, with equivalent results. The primary translation products were assessed by polyacrylamide gel electrophoresis (Laemmli, 1970), in 12% (w/v) or 15% (w/v) acrylamide, followed by autoradiography. The experimentally determined primary IGF-1A translation product demonstrated a mobility of approximately 17,000 daltons, in excellent agreement with the predicted molecular weight of the 153 amino acid precursor, 17,026 daltons. Additionally, the amino-terminal amino acid sequence of this IGF-1A peptide synthesized in vitro was determined and agreed completely with the sequence of the primary translation product predicted from the first in-frame methionine codon (e.g. base pairs 59-61 for IGF-1A, FIG. 5) and not at methionine residues 24 or 27 (e.g. base pairs 128-130 or 137-139, respectively, see FIG. 5). IGF-1A was thus synthesized as a 153 amino acid precursor. Similarly, the experimentally-determined primary IGF-1B translation product migrated on a polyacrylamide gel with a mobility of approximately 22,000 daltons, also in excellent agreement with the predicted molecular weight of the 195 amino acid IGF-1B, 21,841 daltons, as defined by the IGF-1B cDNA sequence. Thus, IGF-1B was produced as a 195 amino acid molecule corresponding to the protein encoded in the synthetic DNA and essentially pure IGF-I gene of the present invention.

Various other examples will be apparent to the person skilled in the art after reading the present disclosure without departing from the spirit and scope of the invention, and it is intended that all such other examples be included within the scope of the appended claims.

REFERENCES

Aviv, H. and Leder, P. (1972) *Proc. Nat'l. Aca. Sci., U.S.A.* 69:1408-1412.

Bell, G. I., Gerhard, D. S., Fong, N. M., Sanchez-Pescador, R. and Rall, L.B. (1985) *Proc. Nat'l. Acad. Sci. U.S.A.* 82:6450-6454.

Biggin, M. D., Gibson, T. J. and Hong, G. F. (1983) *Proc. Nat'l. Acad. Sci., U.S.A.* 80:3963-3965.

Brissenden, J. E., Ullrich, A. and Francke, U. (1984) *Nature (London)* 310:781-784.

Chirgwin, J. M., Przybyla, A. E., Macdonald, R. J. and Rutter, W. J. (1979) *Biochemistry* 24:5294-5299.

Clemmons, D. R., and Shaw, D. S. (1983) *J. Cellular Physiol.* 115:137-142.

Clemmons, D. R., and Van Wyk, J. J. (1981a) *J. Cell Physiol.* 106:361-367.

Clemmons, D. R., and Van Wyk, J. J. (1981b) *J. Clin. Invest.* 67:10-19.

Copeland, K. C., Underwood, L. E. and Van Wyk, J. J. (1980) *J. Clin. Endocrinol. Metab.* 50:690-697.

Davanloo, P. et al. (1984) *Proc. Nat'l Acad. Sci., U.S.A.* 81:2035-2039.

Daughaday, W. H. (1977), Clin. Endocrin. Metal 6:117-135.

Dayhoff, M. O., Barker, W. C. and Hunt, C. T. (1983) *Methods in Enzymol.* 91:524-545.

Gubler, V. and Hoffman, B. J. (1983) *Gene* 25:263-269, Hart, R.P., McDevitt, M.A., and Nevins, J. R. (1985) *Cell* 43:677-683.

Helms, C., Graham, M. Y., Dutchik, J. E. and Olson, M. V. (1985) *DNA* 4:39-49.

Humbel, R. E. (1984) in *Hormonal Proteins and Peptides* ed. Choh Hao Li, Academic Press, Inc., Vol. XII, p. 66-68.

Hylka, V. W., Teplow, D. B., Kent, S. B. H., and Strauss, D. S. (1985) *J. Biol. Chem.* 260:14417-14420.

Jansen, M., van Schaik, F. M. A., Ricker, A. T., Bullock, B., Woods, D. E., Gabbay, K. H., Nussbaum, A. L., Sussenbach, J. S. and Van den Brande, J. L. (1983) *Nature (London)* 306:609-611.

Kwok, S. C. M., Ledley, F. D., Di Lella, A. G., Robson, K. J. H., and Woo, S. L. C. (1985) *Biochemistry* 24:556-561.

Laemmli, U. K. (1970) *Nature* 277:680-685.

Lawn, R.M. et al. (1978) *Cell* 15:1157-1174.

Lehninger, A. L. (1976) *Biochemistry*, 2nd Ed., Worth Publishers, Inc., New York, N.Y. pp72-73, 315-322.

Maniatis, T., Fritsch, E. F., Sambrook, J. (1982) in *Molecular Cloning: A Laboratory Manual*, Cold Spring Harbor Laboratory, pp. 104-107, 374-382.

Marquardt, H., and Todaro, G. J. (1981) *J. Biol. Chem.* 256:6859-6863.

McMaster and Carmichael (1977) *Proc. Nat'l. Acad. Sci. U.S.A.* 74:4835-4838.

Melton, D. A. et al. (1984) *Nuc. Acid Res.* 12:7035-7055.

Nordheim, A. and Rich, A. (1983) *Proc. Nat'l. Acad. Sci., U.S.A.* 74:560-564.

Norrander, J., Kempe, T. and Messing J. (1983) *Gene* 6:101-106.

Pelham, H. R. B. and Jackson, R. J. (1976) *Eur. J. Biochem.* 67:247;256.

Poncz, M. et al. (1982) *Proc. Nat'l. Acad. Sci., U.S.A.* 79:4298-4302.

Rigby et al. (1977) *J. Mol. Biol.* 113:237-251.

Rinderknecht, E. and Humbel, R. E. (1978a) *J. Biol. Chem.* 53:2769-2776.

Rinderknecht, E. and Humbel, R. E. (1978b) *FEBS Lett* 89:283-286.

Rosenfeld, M. G. et al. (1983) *Nature* 304:129-135.

Rubin, J. S., Muriz, I., Jacobs, J. W., Daughaday, W. H. and Bradshaw, R. A. (1982) *Endocrinology* 110:734-740.

Sanger, F., Nicklen, S., and Coulsen, A. R. (1977) *Proc. Nat'l. Acad. Sci., U.S.A.* 74:5463-5467.

Schmid, C. W. and Jelinek, W. R. (1982) *Science* 216:1065-1070.

Schoenle, E., Zapf, J., Humbel, R. E. and Foresch, E. R. (1982) *Nature (London)* 296:252-253.

Southern, E. M. (1975) *J. Mol. Biol.* 98:503-517.

Thomas, P. S. (1980) *Proc. Nat'l. Acad. Sci. U.S.A.* 77:5201-5205.

Tricoli, J. V., Rall, L. B., Scott, J., Bell, G. I., and Shows, J. B. (1984) *Nature (London)* 310:784-786.

Ullrich, A., Berman, C. H., Dull, T. J., Gray, A. and Lee, J. M. (1984) *EMBO J.* 3:361-364.

van Buul-Offers, S. and Van den Brande, J. L. (1980) in *Growth Hormone and Other Biologically Active Peptides* eds. Pecile, A. & Miller, E. E.; p. 103-122; Excerpta Medica, Amsterdam.

Vassilopoulou-Sellin, R. and Phillips, L. S. (1982) *Endocrinology* 110:582-589.

Wahl, G. M., Stein, M. and Stark, G. R. (1979) *Proc. Nat'l. Acad. Sci., U.S.A.* 76:3683-3687.

Wilbur, W. J. and Lipman, O.J. (1983) *Proc. Nat'l. Sci., U.S.A.* 80:726-730.

Wilson, D. M. and Hintz, R. L. (1982) *J. Endocrinol.* 95:59.

Woo, S. L. C. (1979) *Methods in Enz.* 68:389-395.

Young and Davis (1983) *Proc. Nat'l. Acad. Sci., U.S.A.* 35 80:1194-1198.

Zapf, J., Schmid, C. H., and Froesch, E. R. (1984) *J. Clin. Endocrinol. Metal* 13:3-10.

Zumstein, P. P., Luthi, C. and Humbel, R. E. (1985) *Proc. Nat'l. Acad. Sci., U.S.A.* 82:3169-3172.

We claim:

1. A synthetic DNA sequence encoding a preproinsulin-like growth factor-I protein comprising the sequence of amino acids shown in FIG. 2.

2. A synthetic DNA sequence comprising the sequence of nucleotides from about nucleotide 1 to about nucleotide 1136 shown in FIG. 2.

3. A synthetic DNA sequence comprising the sequence of nucleotides from about nucleotide 183 to about nucleotide 767 shown in FIG. 2.

4. A synthetic DNA sequence encoding a mature human IGF-I peptide linked directly at its carboxy-end to the amino terminus of a peptide comprising the following sequence of amino acids:

$NH_2$—Arg Ser Val Arg Ala Gln Arg His Thr Asp Met Pro Lys Thr Gln Lys Tyr Gln Pro Pro Ser Thr Asn Lys Asn Thr Lys Ser Gln Arg Arg Lys Gly Trp Pro Lys Thr His Pro Gly Gly Glu Gln Lys Glu Gly Thr Glu Ala Ser Leu Gln Ile Arg Gly Lys Lys Lys Glu Gln Arg Arg Glu Ile Gly Ser Arg Asn Ala Glu Cys Arg Gly Lys Lys Gly Lys—COOH.

5. A DNA sequence of claim 4 comprising the sequence of nucleotides from about nucleotide 327 to about nucleotide 767 shown in FIG. 2.

6. A synthetic DNA sequence encoding a peptide comprising of the following sequence of amino acids:

$NH_2$—Arg Ser Val Arg Ala Gln Arg His Thr Asp Met Pro Lys Thr Gln Lys Tyr Gln Pro Pro Ser Thr Asn Lys Asn Thr Lys Ser Gln Arg Arg Lys Gly Trp Pro Lys Thr His Pro Gly Gly Glu Gln Lys Glu Gly Thr Glu Ala Ser Leu Gln Ile Arg Gly Lys Lys Lys Glu Gln Arg Arg Glu Ile Gly Ser Arg Asn Ala Glu Cys Arg Gly Lys Lys Gly Lys—COOH.

7. A DNA sequence of claim 6 comprising the sequence of nucleotides from about nucleotide 537 to about nucleotide 767 shown in FIG. 2.

8. A synthetic DNA sequence encoding a peptide comprising of the following sequence of amino acids:

NH₂—Tyr Gln Pro Pro Ser Thr Asn Lys Asn Thr Lys Ser Gln Arg Arg Lys Gly Trp Pro Lys Thr His Pro Gly Gly Glu Gln Lys Glu Gly Thr Glu Ala Ser Leu Gln Ile Arg Gly Lys Lys Lys Glu Gln Arg Arg Glu Ile Gly Ser Arg Asn Ala Glu Cys Arg Gly Lys Lys Gly Lys—COOH.

9. A DNA sequence of claim 8 comprising the following sequence of nucleotides:

5'—TATCAGCCCCATCTACCAACAAGAACA CGAAGTCTCAGAGAAGGAAAGGTTGGC CAAAGACACATCCAGGAGGGGAACAGA AGGAGGGGACAGAAGCAAGTCTGCAGA TCAGAGGAAAGAAGAAAGAGCAGAGG AGGGAGATTGGAAGTAGAATGCTGAAT GCLAGAGGCAAAAAAGGAAAATGA—3'.

10. An essentially intron-free DNA sequence encoding a preproinsulin-like growth factor-I comprising the sequence of amino acids shown in FIG. 6.

11. An essentially intron-free DNA sequence encoding a mature human insulin-like growth factor-I peptide linked directly at its carboxy-end to the amino-terminus of a peptide comprising the following sequence of amino acids:

NH₂—Arg Ser Val Arg Ala Gln Arg His Thr Asp Met Pro Lys Thr Gln Lys Tyr Gln Pro Pro Ser Thr Asn Lys Asn Thr Lys Ser Gln Arg Arg Lys Gly Trp Pro Lys Thr His Pro Gly Gly Glu Gln Lys Glu Gly Thr Glu Ala Ser Leu Gln Ile Arg Gly Lys Lys Lys Glu Gln Arg Arg Glu Ile Gly Ser Arg Asn Ala Glu Cys Arg Gly Lys Lys Gly Lys—COOH.

12. An essentially intron-free DNA sequence encoding extension peptide comprising the following sequence of amino acids:

NH₂—Arg Ser Val Arg Ala Gln Arg His Thr Asp Met Pro Lys Thr Gln Lys Tyr Gln Pro Pro Ser Thr Asn Lys Asn Thr Lys Ser Gln Arg Arg Lys Gly Trp Pro Lys Thr His Pro Gly Gly Glu Gln Lys Glu Gly Thr Glu Ala Ser Leu Gln Ile Arg Gly Lys Lys Lys Glu Gln Arg Arg Glu Ile Gly Ser Arg Asn Ala Glu Cys Arg Gly Lys Lys Gly Lys—COOH.

13. An essentially intron-free DNA sequence encoding a extension peptide comprising the following sequence of amino acids:

NH₂—Tyr Gln Pro Pro Ser Thr Asn Lys Asn Thr Lys Ser Gln Arg Arg Lys Gly Trp Pro Lys Thr His Pro Gly Gly Glu Gln Lys Glu Gly Thr Glu Ala Ser Leu Gln Ile Arg Gly Lys Lys Lys Glu Gln Arg Arg Glu Ile Gly Ser Arg Asn Ala Glu Cys Arg Gly Lys Lys Gly Lys—COOH.

14. A recombinant DNA vector containing a DNA sequence encoding a preproinsulin-like growth factor I protein comprising the sequence of amino acids shown in FIG. 6.

15. An essentially pure DNA molecule comprising the sequence of nucleotides in the IGF-I gene exon 4 shown in FIG. 4.

16. A recombinant DNA vector containing a DNA sequence encoding an essentially pure mature human insulin-like growth factor-I peptide linked directly at its carboxy-end to the amino-terminus of a peptide comprising the following sequence of amino acids:

NH₂—Arg Ser Val Arg Ala Gln Arg His Thr Asp Met Pro Lys Thr Gln Lys Tyr Gln Pro Pro Ser Thr Asn Lys Asn Thr Lys Ser Gln Arg Arg Lys Gly Trp Pro Lys Thr His Pro Gly Gly Glu Gln Lys Glu Gly Thr Glu Ala Ser Leu Gln Ile Arg Gly Lys Lys Lys Glu Gln Arg Arg Glu Ile Gly Ser Arg Asn Ala Glu Cys Arg Gly Lys Lys Gly Lys—COOH.

17. A recombinant DNA vector containing a intron-free DNA sequence encoding an extension peptide comprising the following sequence of amino acids:

NH₂—Arg Ser Val Arg Ala Gln Arg His Thr Asp Met Pro Lys Thr Gln Lys Tyr Gln Pro Pro Ser Thr Asn Lys Asn Thr Lys Ser Gln Arg Arg Lys Gly Trp Pro Lys Thr His Pro Gly Gly Glu Gln Lys Glu Gly Thr Glu Ala Ser Leu Gln Ile Arg Gly Lys Lys Lys Glu Gln Arg Arg Glu Ile Gly Ser Arg Asn Ala Glu Cys Arg Gly Lys Lys Gly Lys—COOH.

18. A recombinant DNA vector containing a intron-free DNA sequence encoding an extension peptide comprising the following sequence of amino acids:

NH₂—Tyr Gln Pro Pro Ser Thr Asn Lys Asn Thr Lys Ser Gln Arg Arg Lys Gly Trp Pro Lys Thr His Pro Gly Gly Glu Gln Lys Glu Gly Thr Glu Ala Ser Leu Gln Ile Arg Gly Lys Lys Lys Glu Gln Arg Arg Glu Ile Gly Ser Arg Asn Ala Glu Cys Arg Gly Lys Lys Gly Lys—COOH.

* * * * *

UNITED STATES PATENT AND TRADEMARK OFFICE
CERTIFICATE OF CORRECTION

PATENT NO. : 4,963,665

DATED : October 16, 1990

INVENTOR(S) : Peter S. Rotwein and Gwen G. Krivi

It is certified that error appears in the above-identified patent and that said Letters Patent is hereby corrected as shown below:

Column 11, line 15, change "an" to "and";

Column 19, line 45, change "prime" to "primer".

Column 20, line 42, following "the", insert -- IGF-1A cDNA. Translation thus begins with the --.

Column 21, line 17, italicize "Clin. Endocrin. Metal";
    line 21, italicize "Gene";
    line 53, insert -- 2 -- so it reads "26";
    line 60, insert -- 2 -- so it reads "253".
Col. 22:
Claim 6, line 57, delete first "of".
Col. 22:
Claim 8, line 2, delete first "of".
Col. 23:
Claim 9, line 11, insert -- C -- so it reads "5'-TATCAGCCCCC";
    line 16, after the G in the 17th position, insert -- A -- so it reads "GAAATGCTGAAT";
    line 17, after first "GC" delete "L".

UNITED STATES PATENT AND TRADEMARK OFFICE
CERTIFICATE OF CORRECTION

PATENT NO. : 4,963,665

DATED : October 16, 1990

INVENTOR(S) : Peter S. Rotwein and Gwen G. Krivi

It is certified that error appears in the above-identified patent and that said Letters Patent is hereby corrected as shown below:

Col. 24, claim 16, line 14, before "DNA sequence", insert --intron-free--.

Signed and Sealed this

Twenty-fifth Day of August, 1992

Attest:

DOUGLAS B. COMER

*Attesting Officer*     *Acting Commissioner of Patents and Trademarks*